United States Patent
Scorvo

(10) Patent No.: US 8,818,825 B1
(45) Date of Patent: Aug. 26, 2014

(54) PATIENT AUTHENTICATION FRAUD PREVENTION SYSTEM AND METHOD

(75) Inventor: Sean Kristofer Scorvo, Lake Oswego, OR (US)

(73) Assignee: Middlegate, Inc., Lake Oswego, OR (US)

( * ) Notice: Subject to any disclaimer, the term of this patent is extended or adjusted under 35 U.S.C. 154(b) by 210 days.

(21) Appl. No.: 13/272,099

(22) Filed: Oct. 12, 2011

Related U.S. Application Data

(60) Provisional application No. 61/516,251, filed on Apr. 1, 2011.

(51) Int. Cl.
 *G06Q 50/00* (2012.01)
 *G06Q 50/22* (2012.01)

(52) U.S. Cl.
 USPC .................................................. 705/3; 705/2

(58) Field of Classification Search
 CPC ..... G06F 19/322; G06F 19/328; G06Q 50/22; G06Q 50/24
 USPC .......................................................... 705/3
 See application file for complete search history.

(56) References Cited

U.S. PATENT DOCUMENTS

| | | | |
|---|---|---|---|
| 5,577,169 A | 11/1996 | Prezioso | |
| 5,706,427 A | 1/1998 | Tabuki | |
| 6,253,186 B1 | 6/2001 | Pendleton, Jr. | |
| 6,421,650 B1 | 7/2002 | Goetz et al. | |
| 7,421,399 B2 | 9/2008 | Kimmel | |
| 7,593,549 B2 | 9/2009 | Reiner | |
| 7,609,862 B2 | 10/2009 | Black | |
| 7,792,774 B2 | 9/2010 | Friedlander et al. | |
| 7,792,776 B2 | 9/2010 | Friedlander et al. | |
| 7,805,391 B2 | 9/2010 | Friedlander et al. | |
| 2006/0274145 A1 * | 12/2006 | Reiner | 348/62 |
| 2012/0078648 A1 * | 3/2012 | Reiner | 705/2 |

OTHER PUBLICATIONS

The Smartcard Alliance, "Medical Identity Theft in Healthcare." web article, Feb. 2010, 5 pages.
Toporoff, Steven. "The 'Red Flags' Rule: What Health Care Providers Need to Know About Complying with New Requirements for Fighting Identity Theft." FTC Bureau of Consumer Protection, May 2009, 6 pages.
Healthcare Technology News, "Data Breaches and Medical Identity Theft on the Rise." May 4, 2010, 3 pages.
Experian, "The Potential Damages and Consequences of Medical Identity Theft and Healthcare Data Breaches," web article, Apr. 2010, 3 pages.
Nordlund, Daniel J. et al., "Patterns of Prescription Opiate Use by Aged, Blind, or Disabled Clients in Washington State," DSHS Research and Data Analysis Division, 8.27fs, Apr. 2005, 12 pages.
Mahon, William J., "Prescription for Peril," periodical, Coalition Against Insurance Fraud, Insight Series, Dec. 2007, 75 pages.

(Continued)

*Primary Examiner* — Hiep V Nguyen
(74) *Attorney, Agent, or Firm* — Law Office of Karen Dana Oster, LLC

(57) ABSTRACT

A patient authentication fraud prevention system as described herein includes a searchable data archive database, a correlation subsystem, and a feedback subsystem. An alternative preferred patient authentication fraud prevention system preferably includes a searchable data archive database, a collection subprogram, a substantiation subprogram, a correlation subprogram, and a feedback subprogram. Also described herein is a computer-implemented patient authentication fraud prevention method.

25 Claims, 12 Drawing Sheets

(56) References Cited

OTHER PUBLICATIONS

Melnick, Glenn A., et al., "California's Emergency Departments: Do They Contribute to Hospital Profitability?" web article, California Health Care Foundation, Jul. 2003, 6 pages.

Sajan, Amin et al., "The Street Value of Prescription Drugs," journal, Canadian Medical Association, CMAJ Jul. 28, 1998;159(2), 4 pages.
Pitts, Stephen R. et al., "National Hospital Ambulatory Medical Care Survey: 2006 Emergency Department Summary," report, USDHHS, National Health Statistics Reports, No. 7, Aug. 6, 2008, 39 pages.

* cited by examiner

PATIENT AUTHENTICATION FRAUD PREVENTION SYSTEM AND METHOD

The present application is an application claiming the benefit of U.S. Provisional Patent Application No. 61/516,251, filed Apr. 1, 2011. The present application is based on and claims priority from this application, the disclosure of which is hereby expressly incorporated herein by reference in its entirety.

BACKGROUND OF INVENTION

Described herein is a patient authentication fraud prevention system and method and, more specifically, a patient authentication fraud prevention system and method that correlates patient identifying input with archived data pertaining to previous patient encounters, presents a graphical display of the results of the correlation as authenticated information to a medical practitioner, and accepts feedback from the medical practitioner as data for use in the correlation process.

According to Centers for Disease Control (CDC) information, the number of emergency department visitors increased by 32% between 1996 and 2006. The number of emergency departments decreased from 4019 to 3833 between 1996 and 2006 (a 4.6% decrease). Emergency departments were visited over 119.2 million times in 2006 and accounted for 50% of the subsequent non-obstetric inpatient admissions to their attached hospitals (equating to 15.3 million admissions). The Emergency Medical Treatment and Active Labor Act (EMTALA) applied to each of the 3833 Emergency Departments accounting for the cited visits and admissions.

Unfortunately, emergency departments are targeted by fraudulent activity because of EMTALA restrictions, and because of the increasing number of patients visiting a decreasing number of emergency departments. Emergency departments see a large volume of patients at a small number of facilities, allowing people to remain relatively anonymous within the patient flow. Overstressed emergency departments, in turn, increasingly act as the gatekeepers to a majority of the hospitals' inpatient resources in the form of hospital admissions. Because EMTALA specifically states that emergency department care cannot be delayed or deferred in order to verify a patient's identity or ability to pay for care, it is common practice for emergency departments to bill patients at a later date. Thus, emergency departments are in a position where they must render care even when a patient states he has forgotten all forms of identifying information. "Forgetting" such identifying information in any other billing-deferred financial transaction would normally block the transaction. However, EMTALA prohibits hospitals from blocking such emergency department transactions.

Fraudulent activity in emergency departments takes the form of providing false or misleading information for the purpose of the emergency department visit and/or providing false or misleading identifying information. The former type of fraud is most commonly witnessed as "drug seeking behavior" (wherein a patient states he has a medical condition that necessitates prescriptions for controlled or habit forming substances). In such cases, the patient often does not have the requisite medical conditions, does not have the condition to the degree noted, or is being treated for the condition by another medical practitioner. The latter type of fraud, providing false or misleading identifying information, is seen when a patient gives identifying information that is either untrue, or true but belonging to another individual (i.e. medical identity theft).

The Federal Trade Commission (FTC) recognizes that medical identity theft is a growing problem. The FTC stated in a 2009 white paper survey that medical identity theft accounts for 5% of all the identity theft. According to industry sources, medical identity theft cost 1.5 million U.S. consumers over $28 billion cumulatively by the end of 2009, and grew in scope by 112% from 2008 to 2009. Because of the magnitude of the problem, combined with specific vulnerabilities, emergency departments face a significant risk of encountering cases of medical identity theft.

It is worth noting that it is not necessary to use a stolen identity to obtain services in an emergency department, as it is possible to simply fabricate an identity. Industry analysis in the realm of identity checks on admitted patients via third party identity verification services revealed that at least 5% of admitted patients had provided fabricated data regarding their identity and/or billing address. Applying this 5% analysis to the 15.3 million admissions that came from the emergency department in 2006, yields an estimated 780,000 fabricated identities and/or addresses provided to emergency departments in 2006. Unfortunately, this figure accounts for just those cases having fabricated identities and/or addresses that were admitted. It is possible that the 5% figure applies to the remainder of the emergency department patient population, adding up to 5.2 million additional fabricated identities and/or addresses to the emergency department patient census in 2006. The total number (5.98 million) of fabricated identities and/or addresses is separate from the number of medical identity thefts transiting the emergency department.

Emergency departments have certain operational limitations that exacerbate the problem of receiving patients with drug seeking behavior. Patients in the emergency department rarely see the same physician twice, making it easier for patients with drug seeking behavior to avoid questions that go along with continuity of care from one care provider. Simultaneously, hospital systems have legal disincentives to communicate information on patients openly and freely because of the Health Insurance Portability and Accountability Act (HIPAA). Thus, emergency departments find it difficult to informally keep other regional departments informed of patients with drug seeking behavior in the area.

Terminology from the following patent references is primarily from the references themselves and is not necessarily equivalent to the terminology used herein.

U.S. Pat. No. 5,706,427 to Tabuki (the "Tabuki reference") discloses an authentication method for networks. The method in the Tabuki reference uses an application server to request a user host to send authentication data to a verification server. The verification result is sent to the application server, and the user is verified based on the result.

U.S. Pat. No. 5,577,169 to Prezioso (the "Prezioso reference") discloses a fuzzy logic entity behavior profiler. The profiler determines behavioral characteristics, establishes norms for each behavior characteristic, and develops a profile score for target entities. The profiler then organizes the target entities by the relative profile scores within peer groups.

U.S. Pat. No. 7,792,774 to Friedlander et al. (the "Friedlander '774 reference"), U.S. Pat. No. 7,792,776 to Friedlander et al. (the "Friedlander '776 reference"), and U.S. Pat. No. 7,805,391 to Friedlander et al. (the "Friedlander '391 reference") detail specific methods to apply probabilities to a conclusion (or "inference") of possible criminal activity by a person. The methods applied probability analysis by taking factual information regarding cohort groups, metadata, etc. and linking them to the original criminal intent inference. The outcome of the Friedlander methods is an overall probability that someone is engaged in criminal behavior, of which identity theft or fraud could be included.

Some verification services are performed by tracking relatively immutable information such as name, date of birth, and social security number. There has also been a growing number of verification services based on identifiers that cannot be forged or forgotten, such as through the use of biometric authenticators (e.g. fingerprints, iris patterns, DNA, etc.). Examples of prior art references that use biometric authenticators include U.S. Pat. No. 7,609,862 to Black (the "Black reference"), U.S. Pat. No. 7,593,549 to Reiner (the "Reiner reference"), and U.S. Pat. No. 7,421,399 to Kimmel (the "Kimmel reference"). These references use biometric authentication that ranges from using initial verification to using verification to both ensure that care plans are administered to the correct patient and to prevent medical fraud.

Prior art examples of prescription drug monitoring systems include U.S. Pat. No. 6,421,650 to Goetz (the "Goetz reference"). The Goetz reference discloses a medication monitoring system and apparatus that takes physician input on drug types prescribed at an encounter and communicates it to other medical practitioners in real time.

U.S. Pat. No. 6,253,186 to Pendleton, Jr. (the "Pendleton reference") discloses a method and apparatus for detecting fraud. The Pendleton reference discloses an example of a complex event processor (or "CEP") system designed to uncover fraud. Such CEP systems are designed to uncover healthcare entity fraud after it has occurred as opposed to preventing fraud's occurrence. The Pendleton reference's system is equally focused on medical practitioners as it is on potentially fraudulent patients, resulting in the system's information not generally being open to the medical practitioners it is monitoring. While monitoring of medical practitioners is necessary for the type of fraud that the described CEPs are meant to detect, it does have the possible antithetic effect of stifling inhibition of fraud by medical practitioners caring for patients with nefarious intent.

BRIEF SUMMARY OF THE INVENTION

Described herein is a patient authentication fraud prevention system and method and, more specifically, a patient authentication fraud prevention system and method that correlates patient identifying input with archived data pertaining to previous patient encounters, presents a graphical display of the results of the correlation as authenticated information to a medical practitioner, and accepts feedback from the medical practitioner as data for use in the correlation process.

Described herein is a patient authentication fraud prevention system accessible by at least one medical practitioner via a medical practitioner interaction subsystem. The system includes a searchable data archive database, a correlation subsystem, and a feedback subsystem. The searchable data archive database is preferably stored in a machine-readable storage medium. The searchable data archive preferably includes stored patient records of data pertaining to patients. The data archive database is preferably accessible by the correlation subsystem and the feedback subsystem. The correlation subsystem is preferably for receiving patient identifying information as input from a first medical practitioner and for correlating the patient identifying information with a corresponding patient record in the data archive database to create authenticated information to be provided to a second medical practitioner (preferably via a medical practitioner interaction subsystem as a graphical display). The feedback subsystem is preferably for receiving feedback data from a third medical practitioner and the received feedback data may then be incorporated into the data archive database. The system may also include a collection subsystem for collecting the patient identifying information from the first medical practitioner via a medical practitioner interaction subsystem, the patient identifying information being at least part of patient identifying input. The system may also include a substantiation subsystem for receiving patient identifying information as input from the first medical practitioner and for substantiating the patient identifying information to create substantiated information (that includes patient identifying information) to be transmitted to the correlation subsystem. The system may also include an alert subsystem for monitoring patient records in the data archive database and providing alert data to set a flag if a predetermined threshold has been met. It should be noted that the first medical practitioner may be the same as the second medical practitioner, the second medical practitioner may be the same as the third medical practitioner, the third medical practitioner may be the same as the first medical practitioner, or the first, second, and third medical practitioners may all be the same medical practitioner. It should be noted that the patient authentication fraud prevention system may be a program residing in a machine-readable storage medium and implementable by a processor.

Also described herein is a patient authentication fraud prevention system that is preferably accessible by at least one medical practitioner via a medical practitioner interaction subsystem. The system preferably includes a searchable data archive database, a collection subprogram, a substantiation subprogram, a correlation subprogram, and a feedback subprogram. The searchable data archive database (which is preferably stored in a machine-readable storage medium) preferably has stored patient records of data pertaining to patients and is preferably accessible by the correlation subprogram and the feedback subprogram. The collection subprogram (which preferably resides in a machine-readable storage medium and is implementable by a processor) is preferably for collecting the patient identifying information from a first medical practitioner via a medical practitioner interaction subsystem. The patient identifying information is preferably at least part of patient identifying input to be transmitted to the substantiation subprogram. The substantiation subprogram (which preferably resides in a machine-readable storage medium and is implementable by a processor), upon receiving patient identifying information from the collection subprogram, is preferably for substantiating the patient identifying information to create substantiated information (which preferably includes patient identifying information) to be transmitted to the correlation subprogram. The correlation subprogram (which preferably resides in a machine-readable storage medium and is implementable by a processor), upon receiving patient identifying information, is for correlating the patient identifying information with a corresponding patient record in the data archive database to create authenticated information to be provided to a second medical practitioner. The feedback subprogram (which preferably resides in a machine-readable storage medium and is implementable by a processor) preferably is for receiving feedback data from a third medical practitioner, the feedback data being incorporated into the data archive database. The system may further include an alert subprogram (preferably residing in a machine-readable storage medium and implementable by a processor) for monitoring patient records in the data archive database and providing alert data to set a flag if a predetermined threshold has been met.

Also described herein is a computer-implemented patient authentication fraud prevention method that includes the steps of: collecting patient identifying information, the patient identifying information being at least part of patient identifying input; receiving the patient identifying input and the patient identifying information, and substantiating at least the patient identifying information to create substantiated information, the substantiated information including the patient identifying information; receiving the substantiated information and the patient identifying information, and correlating at least the patient identifying information with a corresponding patient record in a data archive database to create authenticated information; and receiving feedback data, and incorporating the feedback data into the data archive database. The method may also include the steps of monitoring patient records in the data archive database and providing alert data to set a flag if a predetermined threshold has been met. The method may be controlled by a system processing device.

The foregoing and other objectives, features, combinations, and advantages of the invention will be more readily understood upon consideration of the following detailed description of the invention, taken in conjunction with the accompanying drawings.

BRIEF DESCRIPTION OF THE SEVERAL VIEWS OF THE DRAWINGS

The accompanying drawings illustrate the exemplary systems and methods and/or provide teachings by which the exemplary systems and methods are more readily understood.

FIG. 8 is a screenshot of an exemplary display interface showing authenticated information for a plurality of patients on a medical practitioner interaction subsystem.

FIG. 9 is a screenshot of an exemplary display interface showing detailed authenticated information for a single patient on a medical practitioner interaction subsystem.

DETAILED DESCRIPTION OF THE INVENTION

Figure 1:
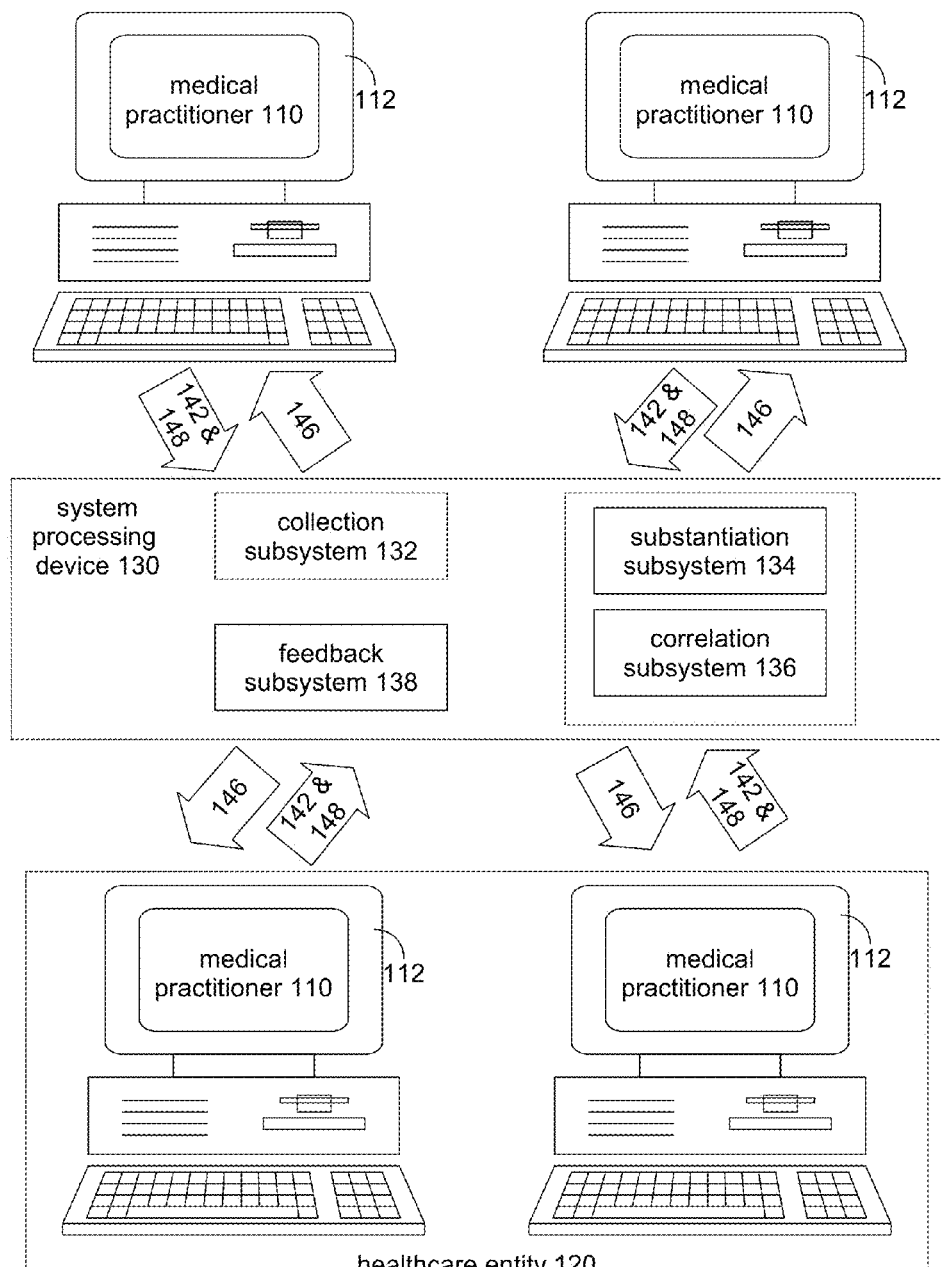
FIG. 1 is a high level block diagram of a preferred exemplary arrangement of constituents of the PAFP system and the communication flow therebetween, the shown constituents including at least one medical practitioner and a system processing device.

Described herein is a "patient authentication fraud prevention system and method" (referred to jointly as the "PAFP system and method," or individually as the "PAFP system" or "PAFP method"). The PAFP system and method is designed to help medical practitioners by providing authenticated information (possibly in combination with substantiated information) pertaining to, for example, a patient's identity, facility use, prescription receipt, and other pertinent alerts (flags) in a manner that is recognizable in a brief visual scan without the need for reading unless further patient analysis is desired on a case-by-case basis. Components of the PAFP system 100 may implement steps of the PAFP method.

Preferred PAFP systems and methods described herein preferably include at least one of four unique features: the ability to correlate patient identifying input (or at least the patient identifying information derived from or associated therewith) with archived data pertaining to previous patient encounters (patient records); the ability to both "substantiate" and "correlate" patient identifying input; the ability to present a graphical display of the results of the correlation (and possibly substantiation) as authenticated information to "medical practitioners" who have the ability to address fraud within the guidelines of federal law; and the ability to accept feedback from the medical practitioners as data that may be used in the correlation process. Preferred PAFP systems and methods allow a medical practitioner to submit patient identifying input obtained from his patient, to receive information in real time that will help him provide appropriate patient care (e.g. refer those patients with objectively identified drug abuse problems to appropriate drug abuse treatment programs) with a high degree of certainty pertaining to fraud issues, and to provide feedback data that can be incorporated back into the PAFP system that can be used to increase the overall accuracy of the PAFP system.

When the PAFP system uncovers fraud, medical practitioners (e.g. emergency department medical practitioners) still perform the federally required (under EMTALA) medical screening exam and stabilize the patient within the guidelines of medical ethics. Medical practitioners, being aware of the fraud, are then free to stop further treatment (and therefore, further expenditures) and avoid providing prescriptions for controlled substances to patients with drug seeking behavior.

As shown in FIGS. 1-4, the PAFP system 100 includes at least one medical practitioner 110 (who may be associated with a healthcare entity 120) functionally associated with (e.g. in communication with) at least one system processing device 130. Each medical practitioner 110 may access the PAFP system 100 (and particularly the system processing device 130) via a medical practitioner interaction subsystem 112 (e.g. a computer). The system processing device 130 preferably includes subsystems including an optional collection subsystem 132, a substantiation subsystem 134 (detailed in FIG. 5), a correlation subsystem 136 (detailed in FIG. 6), and a feedback subsystem 138.

Communications and/or signals between the components of the PAFP system 100 include, but are not limited to patient identifying input 142, substantiated information 144 (which may include substantiated information 144a-c), authenticated information 146 (which may include authenticated information 146a-f), and feedback 148. These communications and/or signals are carried over communication paths.

Before describing the PAFP system, method, and figures, terminology should be clarified. Please note that the terms and phrases may have additional definitions and/or examples throughout the specification. Where otherwise not specifically defined, words, phrases, and acronyms are given their ordinary meaning in the art. Exemplary systems and methods may be better understood with reference to the drawings, but these descriptions are not intended to be of a limiting nature.

The same reference numbers will be used throughout the drawings and description in this document to refer to the same or like parts. The following paragraphs provide some of the definitions for terms and phrases used herein The phrase "medical practitioner" 110 is defined primarily as a person who delivers patient care such as a doctor, nurse, and/or pharmacist. For purposes of understanding the PAFP system 100, however, it is to be understood that the medical practitioner 110 may also include persons who assist in the optimization of care delivery, coordination of healthcare, payment for healthcare delivery, optimization of healthcare, facilitation of patient entry or exit to or from healthcare facilities, and/or computer systems facilitating any of these healthcare providing activities. A medical practitioner 110, therefore, may include, for example, a receptionist, an intake specialist, an orderly, a hospital administrator, an insurance agent, or computer systems related thereto. Although the phrase medical practitioner 110 is used, other people or devices that assist in the medical practitioner's healthcare providing activities would be included. For example, a receptionist or intake specialist may be the "medical practitioner" who actually inputs the patient identifying input 142. Finally, although each patient transaction may be discussed with a single medical practitioner 110, multiple people or devices may be involved.

The phrase "healthcare entity" 120 (or "collecting healthcare entity") is defined as a physical or virtual location that administers, provides, and/or dispenses medical care, medical advice, care coordination, care payment, care optimization, and/or other services or products associated with medical care. Exemplary healthcare entities 120 included, but are not limited to hospitals, emergency departments (either associated with a hospital or as an independent facility), clinics, medical offices, pharmacies, insurance provider facilities, and/or any other physical or virtual location where medical care is administered, provided, and/or dispensed. Medical practitioners 110 may or may not be associated with a healthcare entity 120. Using the broad definition of medical practitioner 110, a healthcare entity 120 most likely has a "medical practitioner" associated with it, although perhaps not a traditional "medical practitioner." (For example, an insurance company may not have an associated doctor, but the insurance agent, for purposes of this disclosure, could be a "medical practitioner" as he assists in the payment for healthcare delivery.)

The phrase "system processing device" 130 is defined as one or more computers, processors, or programs (implantable by a processor) with a primary task of controlling, directing, or implementing the PAFP system and/or method. Coordination between the subsystems described herein (132, 134, 136, 138) may be controlled or orchestrated by the system processing device 130. Alternatively, the subsystems (132, 134, 136, 138) may contain programming such that they function independently (transmitting and/or receiving communications amongst themselves in accordance with the PAFP system 100 described herein), such that together the subsystems (132, 134, 136, 138) function as the system processing device 130.

The phrase "patient identifying input" 142 is defined as the information/data collected by a medical practitioner 110 and input into the collection subsystem 132. The patient identifying input 142 includes, but is not limited to a patient's name, date of birth, social security number, address, insurance information, and/or other personal content.

The term "information" is generally defined as input (including patient identifying information) that has been processed, extracted, and/or analyzed. The term "information" may be preceded by modifiers (e.g. valid, invalid, partially-valid (e.g. valid, but stolen), correlated, or non-correlated). "Validity" is based on whether the patient's identification indicates the existence of a real person. "Correlation" is based on whether the patient's identification can be matched with a patient record in the data archive database 150. Patient identifying input 142 that has been processed and/or analyzed by the substantiation subsystem 134 is considered substantiated information 144. Substantiated information 144 that has been processed and/or analyzed (including being matched with patient records in the data archive database 150) by the correlation subsystem 136 is considered authenticated information 146.

The phrase "patient identifying information" is used to describe specific information that is extracted or derived for the purpose of identifying the patient for the purpose of searching or indexing. In most cases patient identifying information may be the name, birthday, and/or social security number of the patient. The patient identifying information may be part of patient identifying input 142 or substantiated information 144. One of the types of patient identifying information is considered a "piece of information." For example, a name from the patient identifying information of patient identifying input 142 (or substantiated information 144) is a piece of information. All or part of the patient identifying information (or a piece of information) may be used by the substantiation subsystem 134 and/or the correlation subsystem 136 for searching and/or look-up of a particular patient.

The term "data" is used to describe the contents of the data archive database 150 used by the correlation subsystem 136 and populated (at least in part) by feedback data 148 from the feedback subsystem 138. The data may be arranged in patient records. The data (archived data) in the data archive database 150 is preferably further supplemented and enhanced by feedback data 148 obtained from medical practitioners 110 using the feedback subsystem 138. Data may include content similar to the patient identifying input 142 (e.g. patient's name, date of birth, social security number, address, insurance information, and/or other personal content) against which the patient identifying input 142 can be compared. In addition, the data may include content similar to feedback data 148. Feedback data 148 is input by medical practitioners 110 (and/or the medical practitioner interaction subsystems 112) based on medical-decision making and/or patient care plan outcomes from previous patient encounters and may include, for example, time(s), location(s), facilities(s), medical record number(s) (or other visit history content), diagnosis (diagnoses), prescription(s) (e.g. controlled substances), treatment(s), "flags," or any other data that would help a medical practitioner 110 during a patient encounter of that patient.

The term "flag" is defined as an alert pertaining to a patient. The flags may be set by a medical practitioner 110 or by the PAFP system 100 (e.g. by the alert subsystem 160). The medical practitioner 110 may, for example, set a flag pertaining to a patient's behavior. The PAFP system 100 may, for example, set a flag automatically pertaining to the meeting of predetermined thresholds. For example, the PAFP system 100 may include an alert subsystem 160 that sets a threshold pertaining to particular drugs (e.g. any prescription of a habit forming drug or X number of prescriptions of a habit forming drug) or a certain number of encounters within a predetermined period (e.g. two encounters within a one month period). Additional exemplary flags include, but are not limited to colonization by drug resistant bacteria, insurance validity, compliance with court ordered drug programs, existence of care plans, and/or any other data that would help a medical practitioner 110 during a patient encounter of that patient.

The terms "graphics" or "emoticons" are defined as symbols or animations rapidly recognizable by color, shape, or animated activity as representative of a particular level of concern, a particular activity (such as a crime in progress) and/or a level of comfort.

The term "computer" is defined as a device capable of executing instructions or steps and may be implemented as a programmable logic device or other type of programmable apparatus known or yet to be discovered. The computer may have associated memory. The computer may be implemented using a general purpose processor (e.g. microprocessor, controller, microcontroller, or state machine), a digital signal processor (DSP), an application specific integrated circuit (ASIC), a field programmable gate array signal (FPGA) or other programmable logic device, discrete gate or transistor logic, discrete hardware components, or any combination thereof designed to perform the functions described herein. Although shown as a single computer, it should be noted that a computer may be implemented as a plurality of separate computers. Similarly, multiple computers may be combined.

The phrases "communication paths" and "transmission paths" are defined as any type of connection between two nodes on a network (the nodes being, for example, health care entities, systems, subsystems, computers, system processing devices, processing devices, programs, and/or sub-programs that can be used to transmit communications, signals, or other transmissions directly or indirectly thereon). These communications, signals, or other transmissions may be controlled using programs or sub-programs for this purpose. Exemplary communication paths include, but are not limited to wireless networks, the internet, intranets, WAN, LAN, cellular, infrared, and/or any means for connecting nodes that is known or yet to be discovered. Appropriate input mechanisms and/or output mechanisms, even if not specifically described, are considered to be part of the PAFP system 100.

The term "memory" is defined to include any type of computer (or other technology)-readable media (also referred to as machine-readable storage medium) including, but not limited to attached storage media (e.g. hard disk drives, network disk drives, servers), internal storage media (e.g. RAM, ROM, EPROM, FLASH-EPROM, or any other memory chip or cartridge), removable storage media (e.g. CDs, DVDs, flash drives, memory cards, floppy disks, flexible disks), firmware, and/or other storage media known or yet to be discovered. Memory may be transitory or non-transitory, although databases and programs (and subprograms) would most likely be stored in non-transitory memory. Although shown as single units, it should be noted that the memories may be implemented as a plurality of separate memories. Similarly, multiple memories may be combined.

It should be noted that the terms "programs" and "subprograms" are defined as a series of instructions that may be implemented as software (i.e. a computer program, computer program instructions, or computer-readable program code) that may be loaded onto a communication device to produce a machine, such that the instructions that execute on the communication device create structures for implementing the functions described herein or shown in the figures. The systems and subsystems described herein may be implemented by programs and/or subprograms.

When used in relation to signals and/or communications, the terms "provide" and "providing" (and variations thereof) are meant to include standard means of provision including "transmit" and "transmitting," but can also be used for non-traditional provisions as long as the signal and/or communication is "received" (which can also mean obtained). The terms "transmit" and "transmitting" (and variations thereof) are meant to include standard means of transmission, but can also be used for non-traditional transmissions as long as the signal and/or communication is "sent." The terms "receive" and "receiving" (and variations thereof) are meant to include standard means of reception, but can also be used for non-traditional methods of obtaining as long as the signal and/or communication is "obtained." For example, if the feedback data 148 is described as being "transmitted" from a medical practitioner interaction subsystem 112 to a data archive database 150, such "transmission" would also include the feedback data 148 being stored and then "obtained" (fetched) for storage in the data archive database 150.

The term "associated" is defined to mean integral or original, retrofitted, attached, positioned near, and/or accessible by. For example, a feedback subsystem 138 (or component thereof) is associated with a medical practitioner 110 in that it is accessible by the medical practitioner 110. Another example is that the system processing device 130 may be associated with a healthcare entity 120 by being integral therewith. For example, a PAFP system 100 that is implemented by an insurance company (which could be considered a healthcare entity) 120 could be said to have a system processing device 130 that is associated therewith.

Unless specifically stated otherwise, the terms "first," "second," and "third" are meant solely for purposes of designation and not for order or limitation. It should be noted that the terms "may," "might," "can," and "could" are used to indicate alternatives and optional features and only should be construed as a limitation if specifically included in the claims. It should be noted that the various components, features, steps, or embodiments thereof are all "preferred" whether or not it is specifically indicated. Claims not including a specific limitation should not be construed to include that limitation.

It should be noted that, unless otherwise specified, the term "or" is used in its nonexclusive form (e.g. "A or B" includes A, B, A and B, or any combination thereof, but it would not have to include all of these possibilities). It should be noted that, unless otherwise specified, "and/or" is used similarly (e.g. "A and/or B" includes A, B, A and B, or any combination thereof, but it would not have to include all of these possibilities). It should be noted that, unless otherwise specified, the term "includes"

means "comprises" (e.g. a device that includes or comprises A and B contains A and B but optionally may contain C or additional components other than A and B). It should be noted that, unless otherwise specified, the singular forms "a," "an," and "the" refer to one or more than one, unless the context clearly dictates otherwise.

Figure 2:
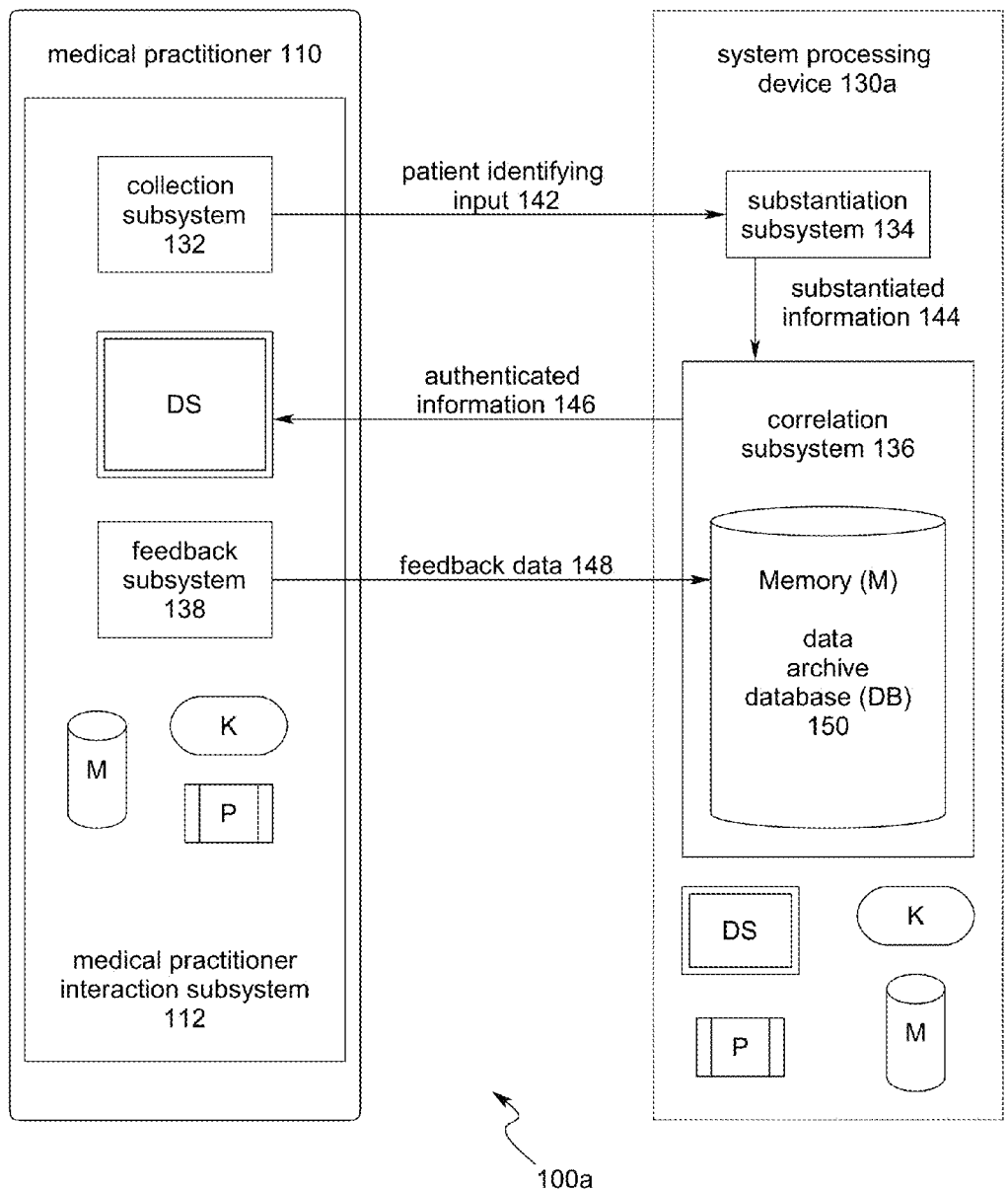
FIG. 2 is a block diagram of a first preferred exemplary alternative PAFP system in which the collection subsystem and the feedback subsystem are associated with the medical practitioner interaction subsystem.
Figure 3:
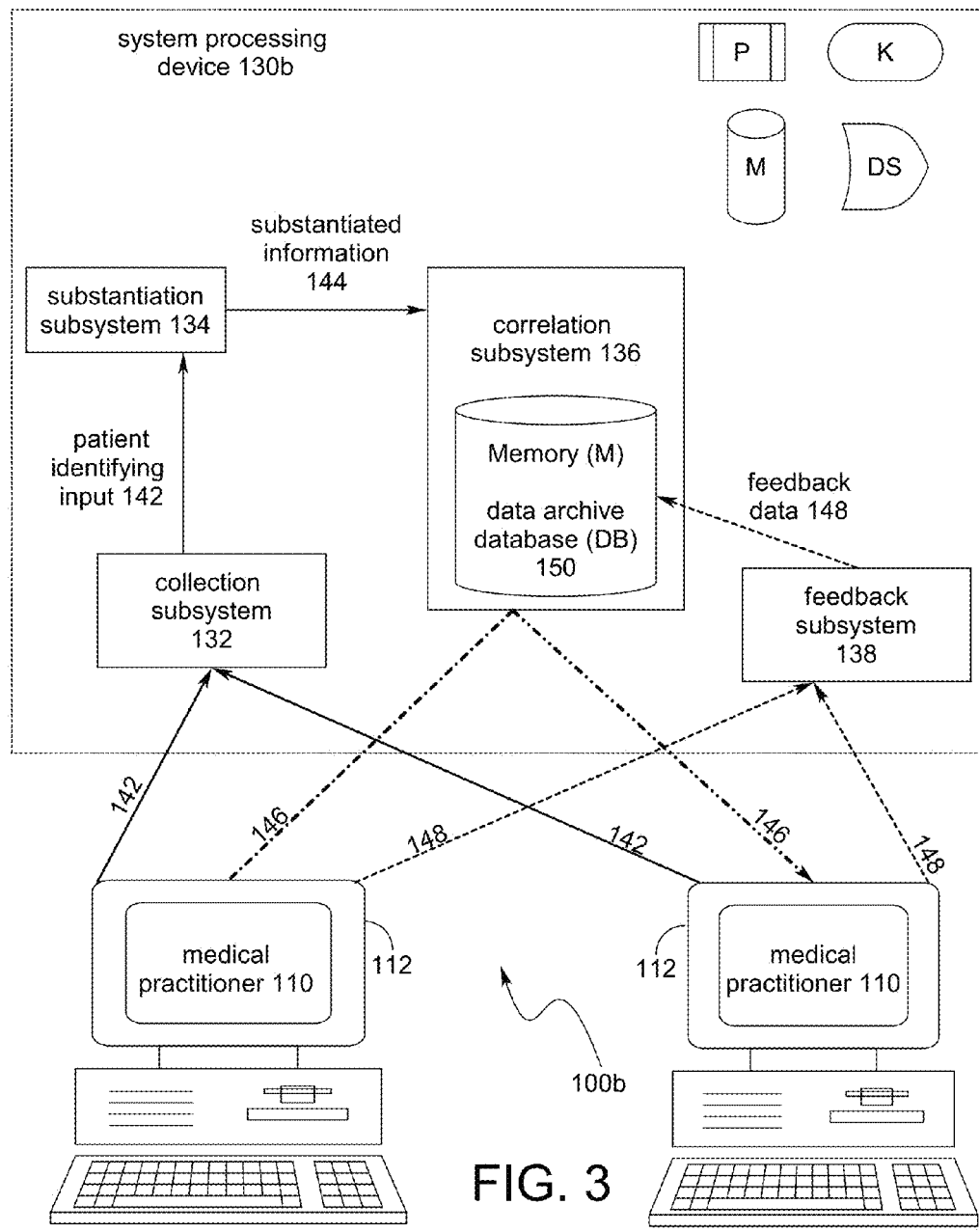
FIG. 3 is a block diagram of a second preferred exemplary alternative PAFP system as it might be implemented in a pure web service implementation.
Figure 4:
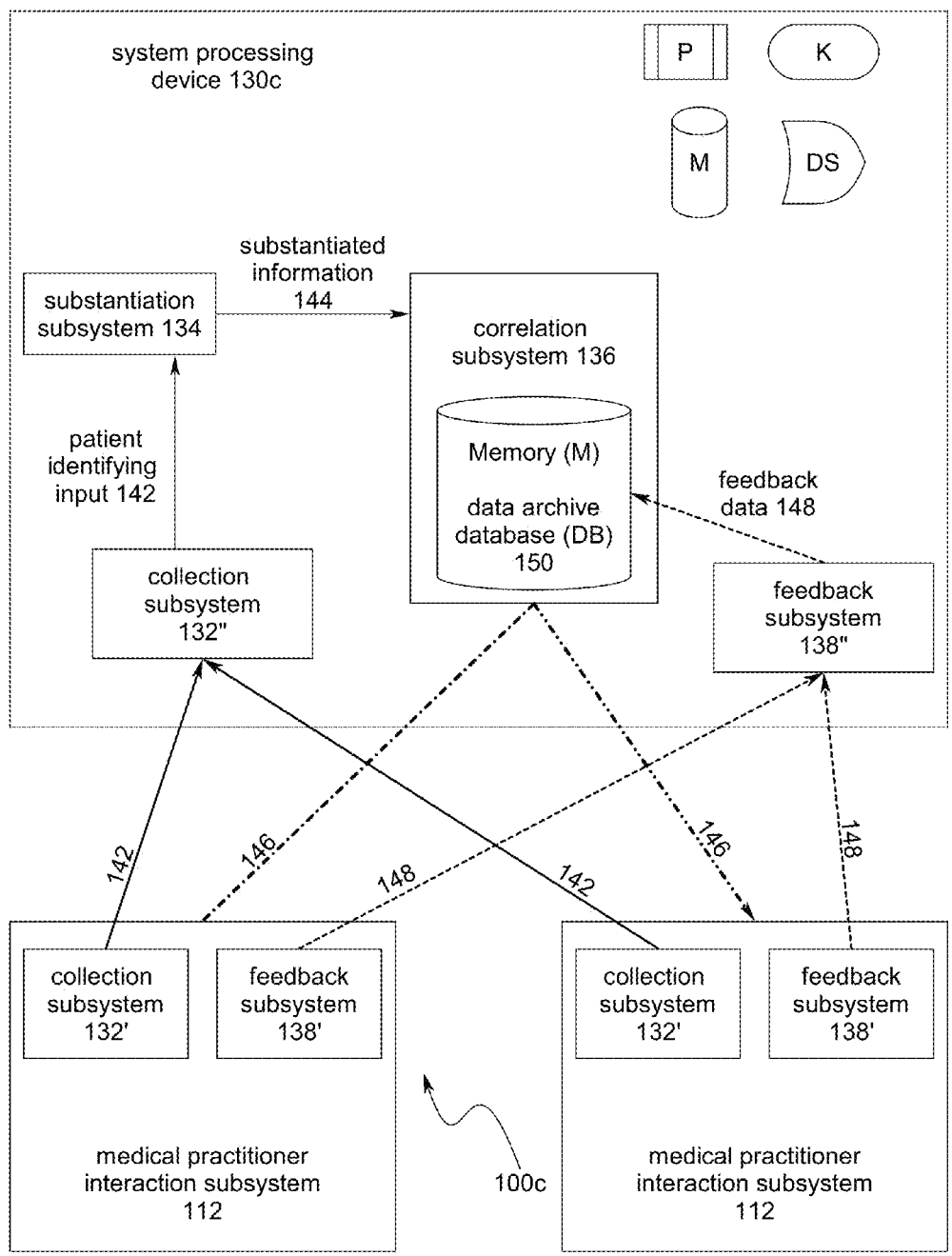
FIG. 4 is a block diagram of a third preferred exemplary alternative PAFP system as it might be implemented in a hybrid web service implementation.

As shown in FIGS. 1-4, the PAFP system (shown as 100 in FIG. 1, 100a in FIG. 2, 100b in FIG. 3, and 100c in FIG. 4, but collectively referred to as the PAFP system 100) is implemented through various subsystems including a collection subsystem 132, a substantiation subsystem 134, a correlation subsystem 136, and a feedback subsystem 138. FIG. 1 shows a high level PAFP system 100 in which medical practitioners 110 and/or healthcare entities 120 (via medical practitioner interaction subsystems 112) transmit and/or receive signals and/or communications from subsystems (132, 134, 136, 138) that are controlled by the system processing device 130 (shown in phantom to emphasize that it may be spread between other components of the PAFP system 100 or implemented as part of the subsystems (132, 134, 136, 138) themselves). The system processing device 130 is shown as 130 in FIG. 1, 130a in FIG. 2, 130b in FIG. 3, and 130c in FIG. 4, but collectively referred to as the system processing device 130. FIG. 2 shows a first preferred alternative PAFP system 100a in which the collection subsystem 132 and the feedback subsystem 138 are implemented (e.g. as program(s), subprogram(s), or standalone computer(s)) as being associated with the medical practitioner interaction subsystem 112. FIG. 3 shows a second preferred alternative PAFP system 100b in which the collection subsystem 132 and the feedback subsystem 138 are implemented (e.g. as program(s), subprogram(s), or standalone computer(s)) associated with the system processing device 130b. The PAFP system 100b of FIG. 3 would be particularly relevant for implementation as a web service in which the medical practitioner 110 logs into a service (e.g. via the Internet) and no program or subprogram is stored on the medical practitioner interaction subsystem 112. FIG. 4 shows a third preferred alternative PAFP system 100c in which a divided collection subsystem (132', 132") and a divided feedback subsystem (138', 138") are implemented (e.g. as program(s), subprogram(s), or standalone computer(s)) partially associated with the medical practitioner interaction subsystems 112 and partially associated with the system processing device 130c. The PAFP system 100c of FIG. 4 is a hybrid system that would allow a sub-portion of the collection system 132' and the feedback subsystem 138' to be stored on each medical practitioner interaction subsystem 112 while the other sub-portion of the collection system 132" and the feedback subsystem 138" is implemented on the system processing device 130c. This would have some of the benefits of the web service implementation of the PAFP system 100b (FIG. 3), but would reduce the burden on the centralized system and possibly allow some (e.g. an initial stage) input and/or feedback at the medical practitioner interaction subsystem 112 if the communication path is not functioning.

The shown PAFP systems 100 are meant to be exemplary and are not meant to exclude alternative arrangements of he components and subsystems. Although not specifically shown, the following are additional exemplary arrangements that are also contemplated: a collection subsystem 132 may be associated with each medical practitioner interaction subsystem 112 and a feedback subsystem 138 may be associated with the central system processing device 130; a feedback subsystem 138 may be associated with each medical practitioner interaction subsystem 112 and the collection subsystem 132 may be associated with the central system processing device 130; a substantiation subsystem 134 may be associated with each medical practitioner interaction subsystem 112; and a correlation subsystem 136 may be associated with each medical practitioner interaction subsystem 112 (and a single data archive database 150 may be associated with the central system processing device 130 or, alternatively, a synchronized copy of the data archive database 150 may be associated with each medical practitioner interaction subsystem 112).

Preferred PAFP systems 100 include multiple medical practitioners 110 (via their respective medical practitioner interaction subsystems 112) that are networked together. This is important to combat the practice of patents visiting multiple medical practitioners 110 and/or multiple healthcare entities 120 to avoid detection. A patient who presents himself to emergency department medical practitioners (or multiple medical practitioners 110 or healthcare entities 120) with the intention of committing fraud or seeking drugs knows that information available to a medical practitioner 110 on a first encounter is incomplete and, therefore, conducive to his intent to perpetuate his fraud or drug seeking behavior. By networking multiple medical practitioners 110, all of whom are providing feedback data 148 into the PAFP system 100 and making authenticated information 146 (which is based, at least in part, on the feedback data 148) to the treating medical practitioner 110 in real time, the patient can be provided with appropriate care.

The Medical Practitioner Interaction Subsystem

It should be noted that the medical practitioner interaction subsystem 112 is preferably a computer that may be used by a medical practitioner 110. The medical practitioner interaction subsystem 112 includes, for example, at least one input mechanism (e.g. a keyboard (K)), at least one processing mechanisms (e.g. processor (P)), at least one memory mechanism (e.g. memory (M)), and at least one display mechanism (e.g. display screen (DS)). The medical practitioner 110 may use the medical practitioner interaction subsystem 112 to input patient identifying input 142, to view authenticated information 146 (preferably presented in an understandable format for the medical practitioner 110 (e.g. in graphic format)), and/or to provide feedback data 148 to be stored in the data archive database 150 of the PAFP system 100. It should be noted that for a particular encounter, multiple medical practitioner interaction subsystems 112 may be used. For example, the patient identifying input 142 may be input at a medical practitioner interaction subsystem 112 at the reception area of a healthcare entity 120, the authenticated information 146 may be viewed by the medical practitioner 110 in the examining room, and the feedback 148 may be input at a medical practitioner interaction subsystem 112 in the medical practitioner's office.

The Collection Subsystem

The collection subsystem 132 may be used for the collection or accumulation of patient identifying input 142 in real time. The collection subsystem 132 may be implemented by a collection program or subprogram that is executed by an associated processor (P) that has access to the collection program or subprogram stored in associated memory (M).

The medical practitioner 110 (e.g. a nurse or receptionist) may conduct an initial interview with the patient to obtain patient identifying input 142 such as, for example, the patient's name, date of birth, social security number, address, insurance information, and/or other personal content. Alternatively, the medical practitioner 110 could conduct his standard input procedure and the collection subsystem 132 could obtain (e.g. mine) the information from other programs. The patient identifying input 142 may also be input using biometrics.

Figure 7:
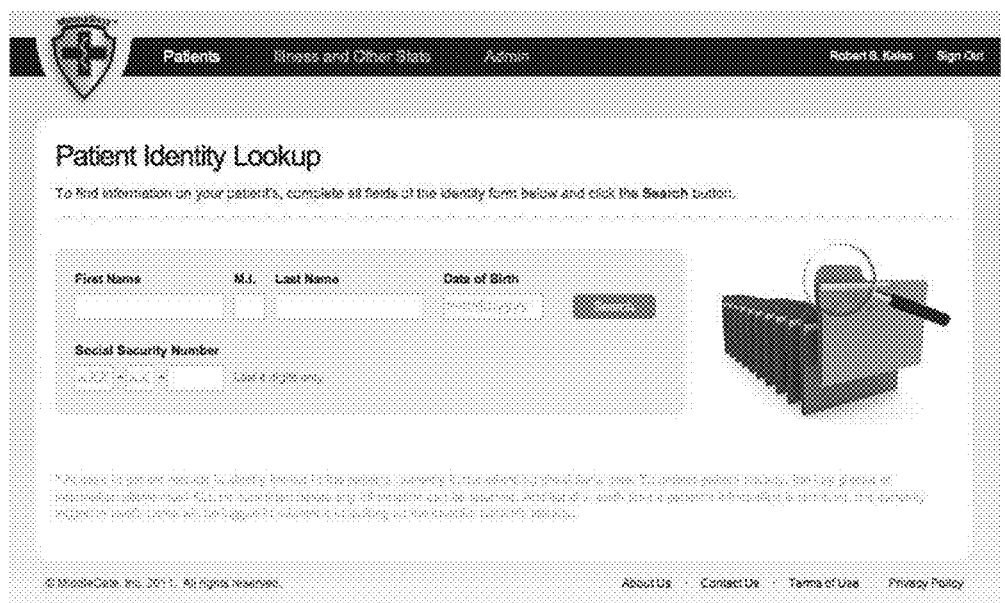
FIG. 7 is a screenshot of an exemplary interface for input of patient identifying input on a medical practitioner interaction subsystem.

FIG. 7 shows an exemplary screenshot of a patient identifying input interface presented to the medical practitioner 110 on the medical practitioner interaction subsystem 112. In this shown example, only three inputs are required (name, date of birth, and social security information). This is meant to be exemplary and additional fields (or fewer fields) could be used.

The following are four exemplary "records" that may be considered to be patient identifying input 142.

| Name | Birthday | SS # | Address | Insurance |
|---|---|---|---|---|
| Bales, Jay M. | Jan. 1, 1972 | 111-11-1111 | 1$^{st}$ Ave., LA, CA | |
| Blaine, Shane M. | Feb. 2, 1973 | 222-22-2222 | 2$^{nd}$ St., LA, CA | AAA22222 |
| Boyln, Gary R. | Feb. 2, 1995 | 333-33-3333 | | |
| Smith, Jerry D. | Apr. 4, 1970 | 444-44-4444 | 4$^{th}$ Cr., LA, CA | AAA44444 |

Although shown in a tabular format, these records may be input individually so that information about a single patient can be returned in real time.

Although shown in FIGS. 2-4 as being a definitive part of the PAFP system 100, the representation of the collection subsystem 132 in FIG. 1 is shown in phantom to indicate that the patient identifying input 142 could be input directly into the substantiation subsystem 134.

The Substantiation Subsystem

Figure 5:
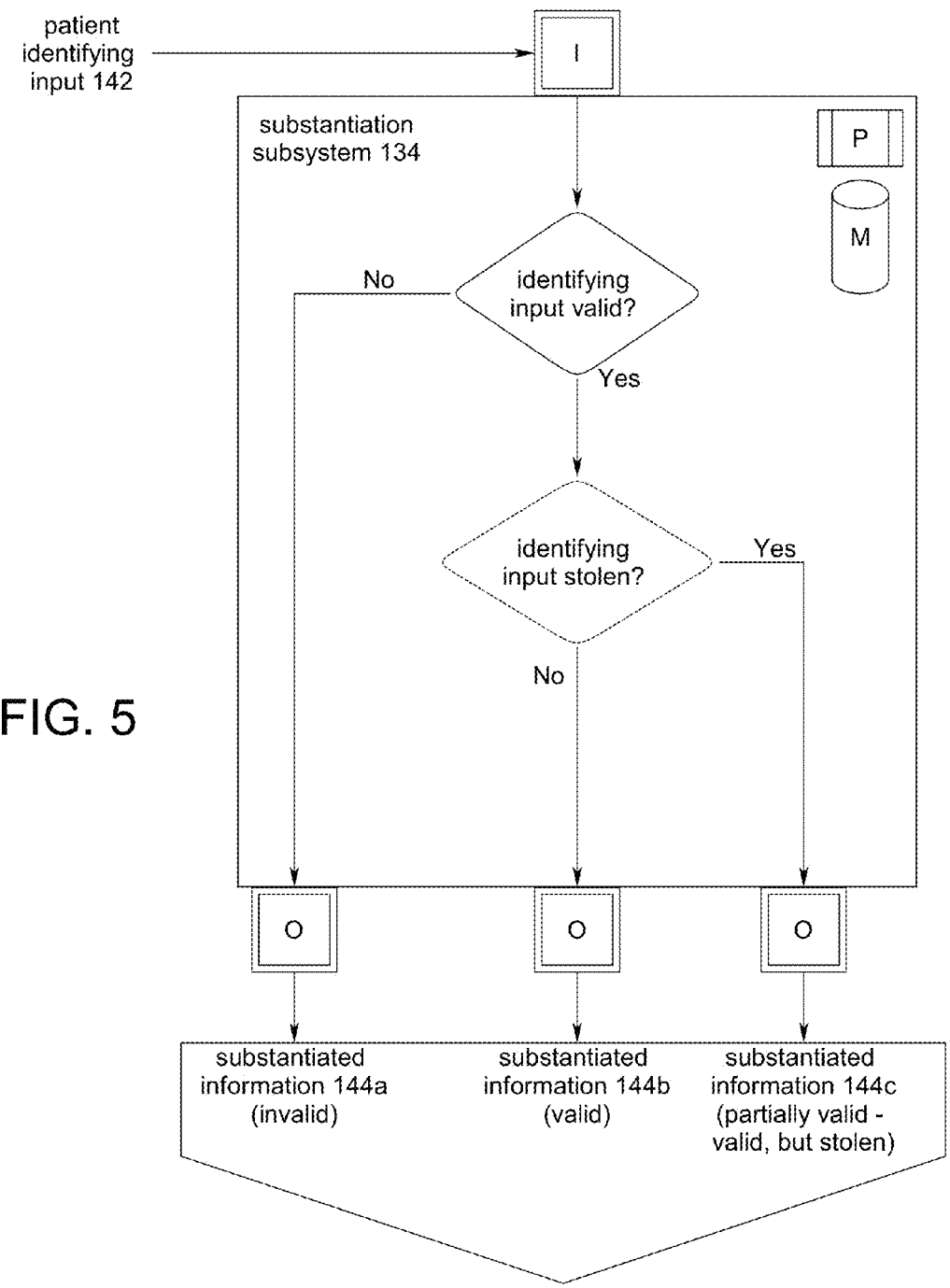
FIG. 5 is a block diagram of preferred exemplary substantiation subsystem and communications therewith.

The purpose of the substantiation subsystem 134 is to substantiate (provide evidence of truth) the patient identifying input 142. The substantiation subsystem 134, as shown in FIG. 5, receives, substantiates, and converts the patient identifying input 142 into substantiated information 144 (which may include substantiated information 144a-c). The substantiation subsystem 134 may be implemented by a substantiation program or subprogram that is executed by an associated processor (P) that has access to the substantiation program (or subprogram) and/or substantiation data stored in associated memory (M). Alternatively, the substantiation subsystem 134 may be implemented through the use of a verification service from one or more third party or affiliated entity (that may be one of the verification services described in the references incorporated herein or another verification service known or yet to be discovered). Another alternative is that the medical practitioner 110 (or healthcare entity 120) can pre-substantiate the patient identifying input 142 and provide the pre-substantiated information directly to the correlation subsystem 136 as substantiated information 144.

The substantiation subsystem 134 reviews the patient identifying input 142 and makes at least one determination about the identity of the patient. These determinations involve comparing the patient identifying input 142 against known databases. For example, social security number databases exist against which the patient identifying input 142 can be checked to verify that the social security number has the same name and/or birthday that was provided by the patient. Other databases may exist pertaining to stolen identification, check cashing fraud, criminal activity and convictions, insurance fraud, and any other known or yet to be discovered verification database. The substantiation subsystem 134 uses one or more of these databases for the primary purpose of substantiating the patient identifying input 142.

As shown in FIG. 5, an exemplary substantiation subsystem 134 reviews the patient identifying input 142 to make two determinations. First, the substantiation subsystem 134 reviews the patient identifying input 142 to determine if it is invalid (substantiated information 144a), valid (substantiated information 144b), and/or valid, but stolen (substantiated information 144c). In the shown example, this is accomplished using two questions: "Is the identifying input valid?" and "Is the identifying input stolen?" These questions may be answered by comparing the patient identifying input 142 to known databases. Instead of, or in addition to, one or both of these questions, additional questions (e.g. "Is this identity associated with criminal activity?" or "Is this identity associated with insurance fraud?") may be answered. There may be separate databases for each question. These questions may be answered using third party or affiliated entity verification services.

The substantiated information 144 may also be augmented with additional content. For example, if an address is not required as patient identifying input 142, the databases associated with the substantiation subsystem 134 may supply the unsupplied content.

After the patient identifying input 142 is passed through the substantiation subsystem 134, the following four exemplary "records" are now substantiated information 144 as follows.

| Name | Birthday | SS # | Address | Insurance |
|---|---|---|---|---|
| Bales, Jay M. | Jan. 1, 1972 | 111-11-1111 | !!! | AAA11111 |
| Blaine, Shane M. | Feb. 2, 1973 | 222-22-2222 | !!! | !!! |
| Boyln, Gary R. | !!! | !!! | | |
| Smith, Jerry D. | Apr. 4, 1970 | 444-44-4444 | 4$^{th}$ Cr., LA, CA | AAA44444 |

Although shown in a tabular format, these records may be input individually so that information about a single patient can be returned in real time. The presence of "!!!" indicates a problem (e.g. information provided was incorrect) or a "flag." Missing information is shown as an empty cell. In this example, Jay M. Bales presented a fraudulent (or incorrect) address that was flagged, but his insurance information was completed by the substantiation subsystem 134. Shane M. Blaine's address and insurance information was flagged as fraudulent (or incorrect). Gary R. Boyln provided a fraudulent identification and the other information was not provided by the substantiation subsystem 134. Mr. Boyln's information most likely would fall into the invalid substantiated information 144a category. Jerry D. Smith's information appears to be valid substantiated information 144b.

Once the substantiation subsystem 134 has sorted the substantiated information 144, some or all of the substantiated information 144 is sent to the correlation subsystem 136. In the shown example, all the substantiated information 144 is sent to the correlation subsystem 136. Alternative substantiation subsystems 134 might send the invalid substantiated information 144a directly to the medical practitioner interaction subsystem 112 without additional correlation (e.g. if the patient identifying input 142 is invalid, it may not be correlated). Other alternative substantiation subsystems 134 might send both the invalid substantiated information 144a and the valid, but stolen substantiated information 144c directly to the medical practitioner interaction subsystem 112.

The Correlation Subsystem

The purpose of the correlation subsystem 136 is to correlate the substantiated information 144. This is significantly different than "substantiating." Whereas "substantiating" relates to the truth of the patient identifying input 142, "correlating" relates to providing information about behaviors, problems, and other information that the medical practitioner 110 might need to know about this particular patient regardless of whether the patient identifying input 142 is true or false. The correlation subsystem 136 allows a medical practitioner 110 who has not seen a patient before to have crucial information about the patient in real time. The correlation subsystem 136 may be implemented by a correlation program or subprogram that is executed by an associated processor (P) that has access to the correlation program or subprogram stored in associated memory (M) (that may be the same as the shown memory or a separate memory).

Figure 6:
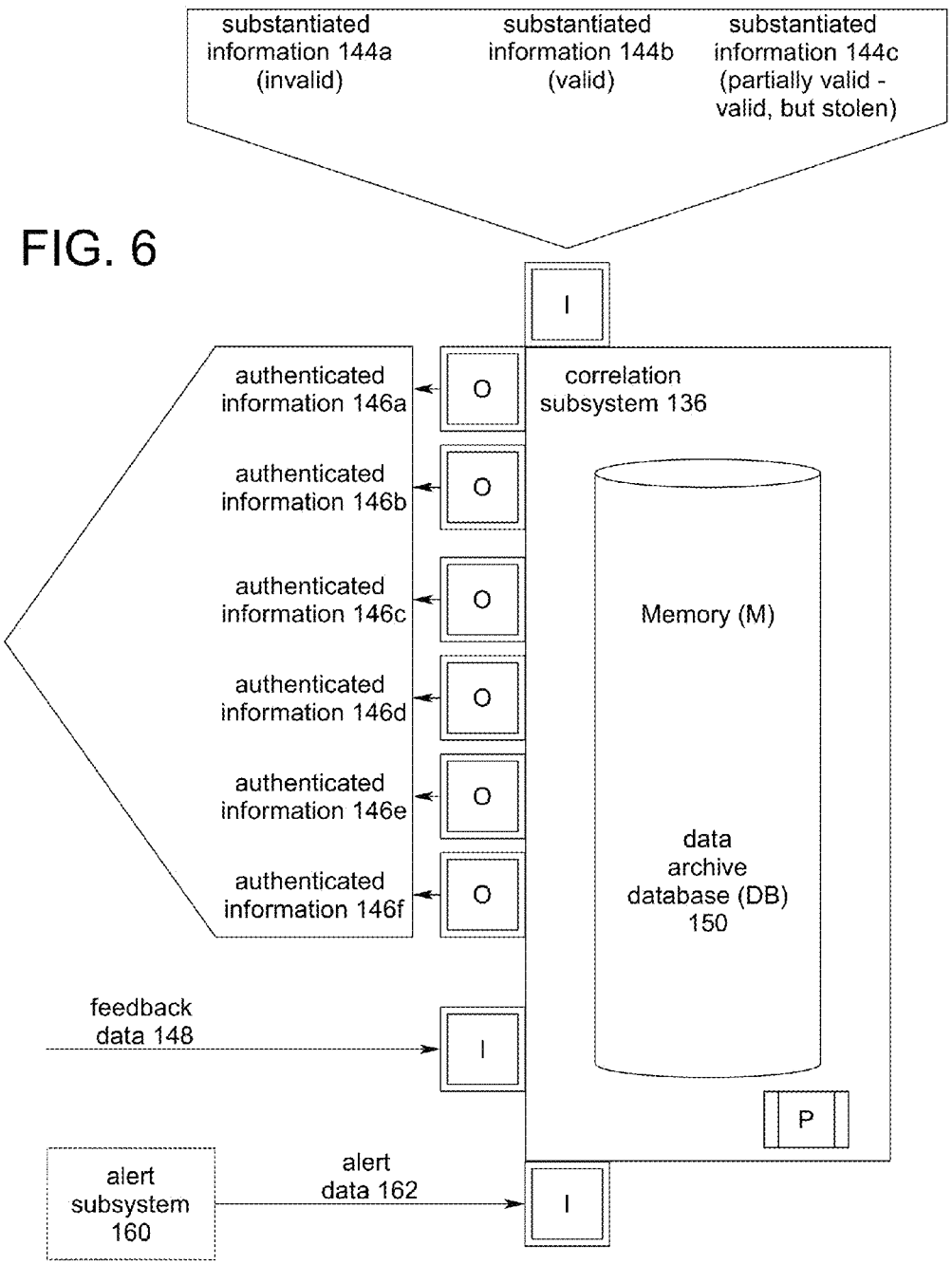
FIG. 6 is a block diagram of preferred exemplary correlation subsystem and communications therewith.

The exemplary correlation subsystem 136, as shown in FIG. 6, receives the substantiated information 144 from the substantiation subsystem 134 and determines if there is matching (correlating) archived data (patient records) stored in the data archive database 150 stored in memory (M). If a matching patient record is present it can be correlated (linked) with the substantiated information 144 (correlated). On the other hand, if a matching patient record is not present, then the substantiated information 144 is non-correlated. As will be discussed, the data archive database 150 includes data from previous healthcare entity 120 visits provided by medical practitioners 110 through the feedback subsystem 138. The data archive database 150 may also include "flags" from the alert subsystem 160.

The correlation subsystem 136 preferably correlates the substantiated information 144 (or at least the valid substantiated information 144b) and links it with archived data (the patient record in the data archive database 150) to create authenticated information 146. In the shown example, if the patient record is not present in the data archive database 150 (non-correlated), then just the substantiated information 144 is provided as authenticated information 146. FIG. 6 shows six examples of authenticated information 146:

invalid, non-correlated authenticated information 146a;
invalid, correlated authenticated information 146b;
valid, non-correlated authenticated information 146c;
valid, correlated authenticated information 146d;
valid, but stolen, non-correlated authenticated information 146e; and
valid, but stolen, correlated authenticated information 146f.

It should be noted that some systems may not correlate certain types substantiated information 144 (e.g. invalid substantiated information 144a and/or valid, but stolen substantiated information 144c) because such information may be not be in the data archive database 150 or it may be inaccurate. On the other hand, if the patient identifying input 142 had been previously fabricated and entered into the system (and is therefore invalid substantiated information 144a), there may be value in determining if there are other problems (e.g. behavioral issues and/or drug seeking behavior). Similar arguments may be made correlating for other types of substantiated information 144 (e.g. valid, but stolen substantiated information 144c). In this example, if the invalid substantiated information 144a and/or valid, but stolen substantiated information 144c is/are not correlated by the correlation subsystem 136, then the only authenticated information that would be output from the correlation subsystem 136 would be valid, non-correlated authenticated information 146c and valid, correlated authenticated information 146d.

Although not shown, it should be noted that the correlation subsystem 136 may be used alone (without the substantiation subsystem 134). In such a situation, the correlation subsystem 136 would use at least a portion of the patient identifying input 142 as input (patient identifying information).

The shown data archive database 150 is shown as associated directly with the correlation subsystem 136 and accessible by the feedback subsystem and/or the optional alert subsystem 160. Alternative PAFP systems 100 could have a standalone data archive database 150 (possibly associated with the system processing device 130) that is accessible by the feedback subsystem and/or the optional alert subsystem 160. Still other PAFP systems 100 could have a synchronized copy of the data archive database 150 that is associated with each medical practitioner interaction subsystem 112. The system processing device 130 is populated using data.

The data in the data archive database 150 may have been provided (at least in part) by the substantiated information 144, the feedback subsystem 138, and/or the alert subsystem 160. The data (archived data) in the data archive database 150 is preferably further supplemented, updated, and/or enhanced by data obtained from the substantiation subsystem 134 (e.g. new patent information), the feedback subsystem 138, and/or "flags" raised by the alert subsystem 160. The data from the substantiation subsystem 134 may be provided indirectly by the feedback subsystem 138. Patient identifying input 142 may be provided directly to the data archive database 150 or via one of the other subsystems.

The data in the data archive database 150 is preferably "searchable." This may be accomplished, for example, by arranging the data in the data archive database 150 in "records" (e.g. patient records) and indexing the records based on, for example, at least one patient identifying datum (e.g. name, birthday, or social security number). Alternatively, the records may be indexed based on more than one (or any) patient identifying data. This multiple indexing is useful because if some records (or data in the records) and/or information (or a piece of the information) are missing, alternative "search terms" (the piece(s) of information) can be used. Information to be correlated (e.g. the patient identifying input 142 and/or substantiated information 144) preferably includes at least one piece of patient identifying information (that may be part of, extracted from, and/or derived from the patient identifying input 142 and/or substantiated information 144) that can be "looked up" (e.g. used as a search term) to find a corresponding indexed record in the data archive database 150 that has patient identifying data that corresponds to the at least one piece of patient identifying information. If the piece(s) (e.g. the name, birthday, and/or social security number) of patient identifying information input into the correlation subsystem 136 is found to have corresponding data (e.g. the same name, birthday, and/or social security number) in the data archive database 150, then the information is "correlated" (e.g. linked) to an associated patient record in the data archive database 150. If the piece(s) of patient identifying information input into the correlation subsystem 136 is not found in the data archive database 150, then the information is "non-correlated."

The alert subsystem 160 (FIG. 6) is shown in this example as a separate subsystem that has the primary purpose of providing alerts (alert data 162) based on data in the data archive database 150. The alert subsystem 160 may be implemented by an alert program or subprogram that is executed by an associated processor (P) that has access to the alert program or subprogram stored in associated memory (M). Although shown as its own subsystem, the alert subsystem 160 could be, for example, part of the correlation subsystem 136. The alert subsystem 160 may be programmed to provide alerts based on predetermined factors or thresholds. Predetermined factors may include the prescription of certain drugs, the exhibition of certain behaviors, previous indications of fraud, previous indications of drug seeking indicators, whether a care plan template has been completed (an alert would be issued if it had not been completed), and any other data that would be particularly relevant to a medical practitioner 110 providing care. Predetermined thresholds are set to provide alerts to factors that, although alone might not be problematic, taken together or cumulatively are problematic. For example, predetermined thresholds might be set pertaining to a certain number of prescriptions of a habit forming drug, a certain number of encounters within a predetermined period (e.g. two encounters within a one month period), or any other factors that might not be apparent to a lone medical practitioner 110. The alert subsystem 160 is preferably set to monitor and/or analyze the data in the data archive database 150 continuously, on a periodic basis (e.g. every hour, once a day, or once a week), automatically based on certain events (e.g. upon receipt of new feedback data 148, when a patient record is accessed by the correlation subsystem 136, or when the data archive database 150 is not being accessed by other subsystems), or upon manual actuation. Upon finding that one of the predetermined thresholds has been met for a particular patient record, the alert subsystem 160 sends alert data 162 to that patient record and modifies the record to include the appropriate flag that will preferably be graphically represented when the record is displayed. The alert subsystem 160 may be implemented by an alert program or subprogram that is executed by an associated processor (P) that has access to the alert program or subprogram stored in associated memory (M).

The following table represents an example of archived data that may be present in the data archive database 150. The archived data is arranged in "records" (shown as lines of the table) for each patient.

The authenticated information 146 (and, if they are not correlated, the invalid substantiated information 144a and/or valid, but stolen substantiated information 144c) is then sent to the medical practitioner interaction subsystem 112.

The Feedback Subsystem

The primary purpose of the feedback subsystem 138 is to allow a medical practitioner 110 to produce and input new data into his medical practitioner interaction subsystem 112 as feedback data 148 that is incorporated back into the data archive database 150 to increase the overall accuracy of the PAFP system 100. (Incorporation can include, for example, adding the feedback data as new data to a patient record where there was no data previously, updating or correcting previous data that was inaccurate or incomplete with the feedback data, augmenting previous data with the addition of the feedback data to the patient record, or otherwise enhancing the accuracy of the data in the data archive database 150.) This is a significant improvement over known systems. It is more than just archiving medical files. The feedback subsystem 138 asks specific questions to a medical practitioner 110 about certain behaviors (e.g. violence, drug seeking) and then incorporates the answers (the feedback data 148) with the patient's other data (e.g. identification data) so that future encounters with this patient by other medical practitioners 110 can have the benefit of the current medical practitioner's immediate knowledge and impressions about this patient. The more medical practitioners 110 see this patient, the more accurate the PAFP system 100 becomes. The feedback subsystem 138 may be implemented by a feedback program or subprogram

| Name | Birthday | SS # | Address | Insurance | Behavior | Thresh | Rx |
|---|---|---|---|---|---|---|---|
| Bales, Jay M. | Jan. 1, 1972 | 111-11-1111 | !!! | AAA11111 | N | N | N |
| Blaine, Shane M. | Feb. 2, 1973 | 222-22-2222 | !!! | AAA22222 | Y | Y | Y |
| Boyln, Gary R. | !!! | !!! | | | | | |
| Smith, Jerry D. | Apr. 4, 1970 | 444-44-4444 | 4$^{th}$ Cr., LA, CA | AAA44444 | N | N | Y |

The Behavior column might represent flags set by the medical practitioner 110 relating to patient behavior (e.g. violence) with "Y" meaning that there was a problem (flag) and "N" meaning that there were not problems (no flag). The Threshold column might represent flags set by the alert subsystem 160 relating to meeting predetermined thresholds (e.g. a certain number of visits within a certain time period) with "Y" meaning that there was a problem (flag) and "N" meaning that there were not problems (no flag). The Rx column might represent flags set by either the medical practitioner 110 or the alert subsystem 160 relating to drug seeking behavior (e.g. behavior exhibited by the patient, a particular prescription, or a certain number of prescriptions of certain drugs) with "Y" meaning that there was a problem (flag) and "N" meaning that there were not problems (no flag). Some of the columns might trigger the same graphical representation for display to the medical practitioner 110. For example, certain flags set by the alert subsystem 160 might be displayed as drug seeking behavior the same as certain flags set by the medical practitioner 110. Missing information is shown as an empty cell. This table is meant to be exemplary and is necessarily incomplete. The actual data archive database 150 might include more columns and/or more information in each column.

Figure 8:
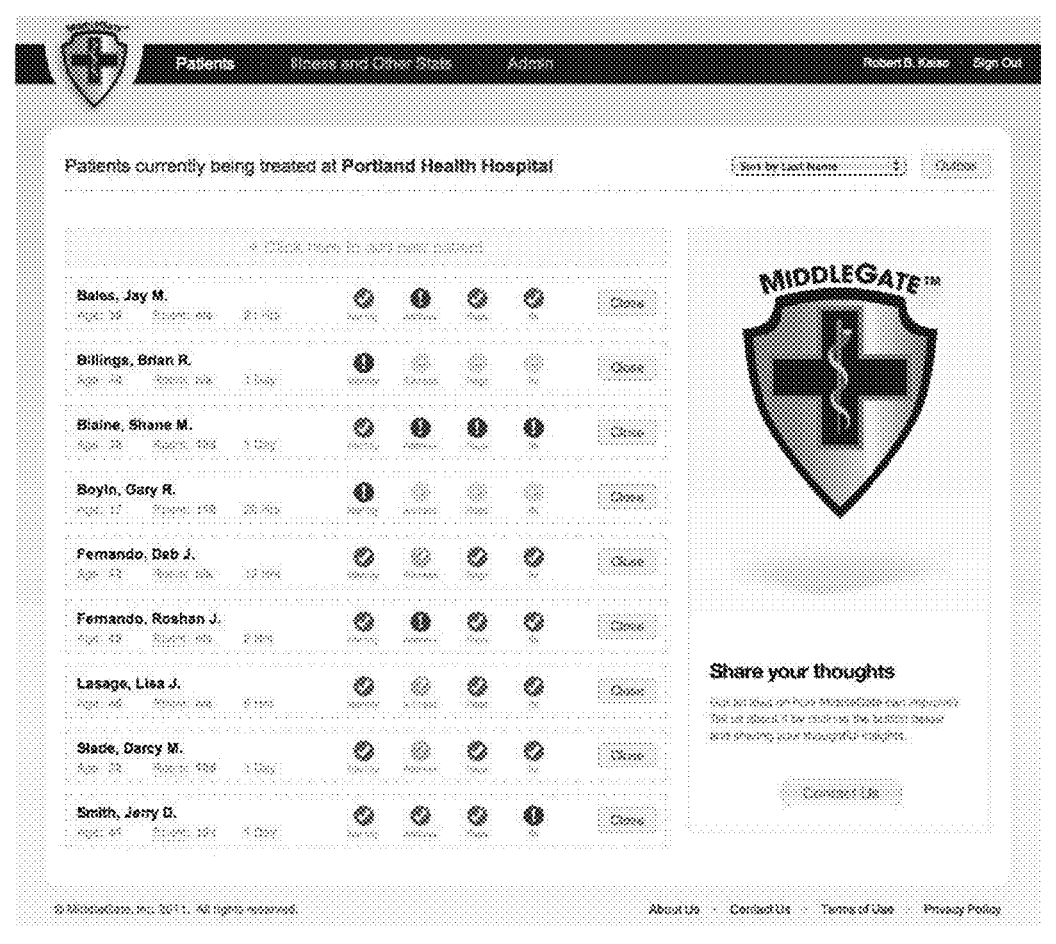

Based on the information from the table above, FIG. 8 could be generated and displayed on the medical practitioner interaction subsystem 112.

that is executed by an associated processor (P) that has access to the feedback program or subprogram stored in associated memory (M).

Figure 10:
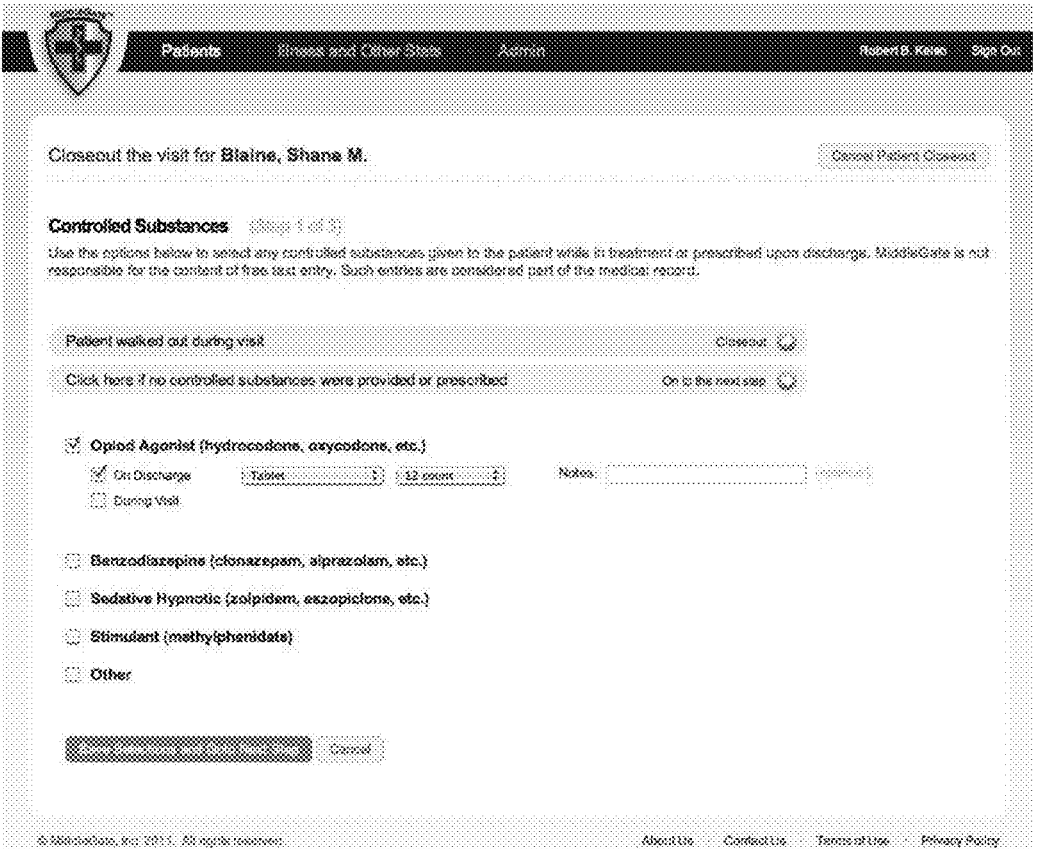
FIG. 10 is a screenshot of an exemplary display interface for input of feedback data from a medical practitioner on a medical practitioner interaction subsystem.

FIG. 10 shows an exemplary screenshot of a feedback input interface presented to the medical practitioner 110 on the medical practitioner interaction subsystem 112 upon completion of a patient-medical practitioner encounter (interaction). The medical practitioner 100 is prompted by the feedback subsystem 138 to provide information regarding the dispensation and/or receipt of prescription for controlled substances, encountering of any behavioral or medical issues warranting flagging. For example, the medical practitioner 110 may be presented with questions, the answers (feedback data 148) to which will be incorporated into the data archive database 150 so that the additional data that can be used to increase the overall accuracy of the PAFP system 100. The questions may be directed to patient diagnosis(es), prescription(s), treatment(s), "flags," recommended care plan, or any other data that would help a medical practitioner 110 during a patient encounter of that patient. In addition, some feedback data 148 may be automatically supplied by the medical practitioner interaction subsystem 112. For example, the time(s), location(s), facilities(s), medical record number(s) may be automatically provided as feedback data 148 depending on the network's ability to auto-populate the information into the feedback subsystem. The feedback subsystem 138 may also keep a numerical tally of the number of encounters within predetermined periods (e.g. how many times a patient saw a medical practitioner 110 in the past week, month, or year).

The following table represents an example of archived data that may be present in the data archive database 150 after new patient encounters with Jay M. Bales, Gary R. Bolyn, and Robert A. Teinlein all at different healthcare entities 120.

| Name | Birthday | SS # | Address | Insurance | Behavior | Thresh | Rx |
|---|---|---|---|---|---|---|---|
| Bales, Jay M. | Jan. 1, 1972 | 111-11-1111 | 1<sup>st</sup> Ave., LA, CA | AAA11111 | N | N | N |
| Blaine, Shane M. | Feb, 2, 1973 | 222-22-2222 | !!! | AAA22222 | Y | Y | Y |
| Boyln, Gary R. | !!! | !!! | | | N | Y | N |
| Smith, Jerry D. | Apr. 4, 1970 | 444-44-4444 | 4<sup>th</sup> Cr., LA, CA | AAA44444 | N | N | Y |
| Teinlein, Robert A. | May 5, 1966 | 555-55-5555 | 5<sup>th</sup> Dr., LA, CA | AAA55555 | Y | N | N |

20

Although shown in a tabular format, these records may have been input individually so the information about a single patient is always current. In this example, Jay M. Bales has presented evidence that his originally provided address was correct and, therefore, the flag has been removed. Mr. Bales' information would probably be classified as valid, correlated authenticated information 146d. Gary R. Boyln's identification has still not been verified (and is probably fraudulent), but he has met a predetermined threshold (perhaps number of visits) so the alert subsystem 160 set a flag. On the other hand, the medical practitioner 110 did not observe behavioral (e.g. violence). Mr. Boyln's information would probably be classified as invalid, correlated authenticated information 146b. Mr. Robert A. Teinlein is a new patient, but his information has now been added to the data archive database 150. Although the medical practitioner 110 flagged Mr. Teinlein's behavior (e.g. violent or abusive), his information most likely would fall into the valid, correlated authenticated information 146d.

The data archive database 150 is shown as being associated with the correlation subsystem 136. It should be noted that alternative embodiments could have a standalone data archive database 150 or a data archive database 150 associated with the feedback subsystem 138. Regardless of physical location, the data archive database 150 is functionally accessible by both the correlation subsystem 136 and the feedback subsystem 138. Further, preferred systems use a centralized data archive database 150 accessible by a plurality of medical practitioner interaction subsystems 112. The correlating subsystem 136 may be a single correlation subsystem 136 or a plurality of correlation subsystems 136 each having access to the data archive database 150. Yet another preferred system would have multiple data archive databases 150 that would be synchronized so that feedback data 148 from medical practitioners 110 at different locations can be shared.

Graphical Presentation

One feature of the PAFP systems 100 described herein is that it presents information in an efficient and convenient manner for medical practitioners 110. There is no need to lookup a patient's file (assuming it is available) and review the file in detail during an emergency. Presenting authenticated information 146 in a graphical and easy to understand manner saves the medical practitioner 110 time, but still allows the medical practitioner 100 to individualize the treatment plan on a case-by-case manner regarding medications prescribed, treatments initiated, follow up recommended, or even the contact of law enforcement within the guidelines of EMTALA, HIPAA, and FTC Red Flag Rule laws.

A patient who presents himself to emergency department medical practitioners with the intention of committing fraud or seeking drugs knows that there is no time for a detailed analysis of his file (assuming the record is available) and counts on the time limitations to perpetuate his fraud or drug seeking behavior. Using the PAFP system 100 with the graphical user interface allows a medical practitioner 110 to act appropriately to curtail fraud in a manner compliant with laws specific to the healthcare field.

One of the ways in which the information is presented in an efficient and convenient manner is by assigning graphics to key indicators of fraud (e.g. identity verification, address verification, prescription receipt, behavioral flags, identity theft, and any other information that would be of interest to a medical practitioner 110). These graphics may be used in user interfaces (e.g. screenshots) that present information pertaining to multiple patients (e.g. FIG. 8), that present information pertaining to a single patient (e.g. FIG. 9), and/or that allows a medical practitioner 110 to provide feedback (e.g. FIG. 10, although this figure does not show a significant use of graphics).

Figure 9:
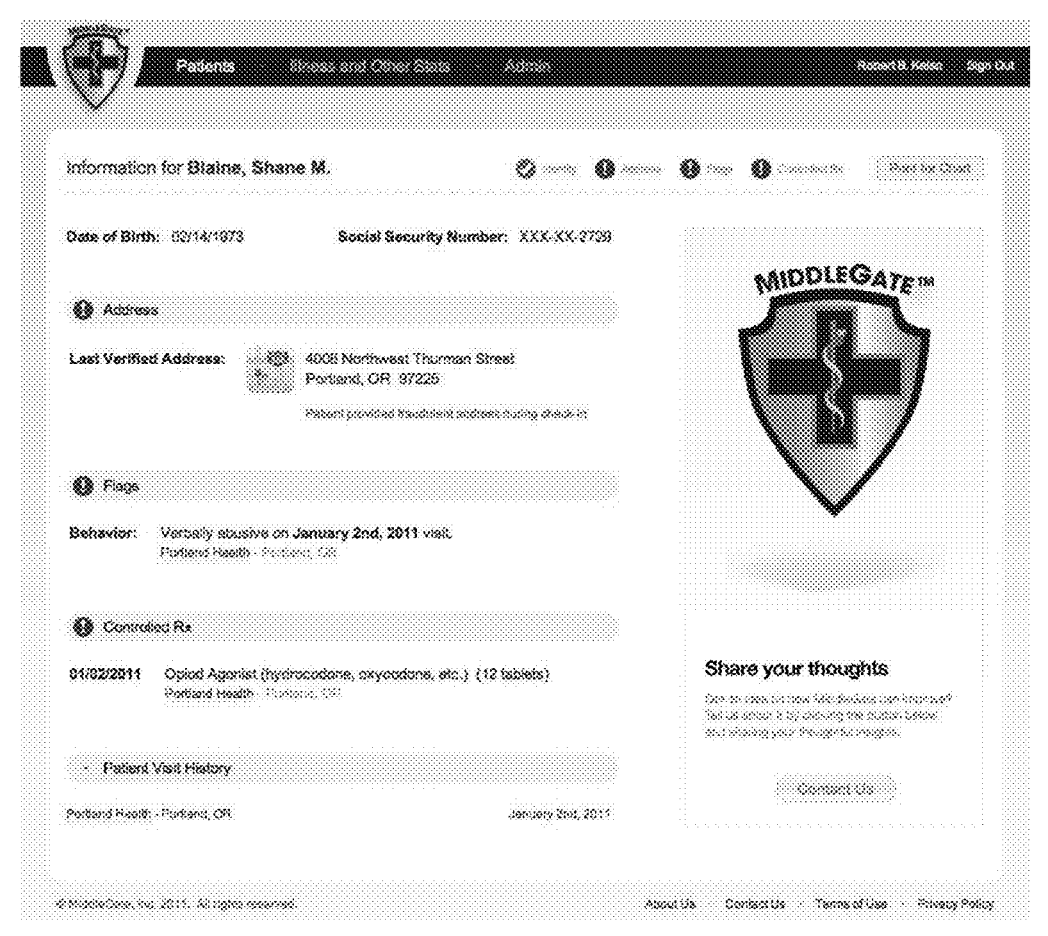

FIGS. 8 and 9 show exemplary of screenshots of graphical presentations for the medical practitioner 110 on the medical practitioner interaction subsystem 112. These figures show an exemplary manner in which the PAFP system 100 may present a medical practitioner 110 who is treating an individual patient with information with real-time relevant information pertaining to the validity of the patient's identity, flags (e.g. those pertaining to behavior), and drug-seeking content. Green checkmarks clearly indicate to the medical practitioner 110 that there is "no problem." A yellow question mark indicates to the medical practitioner 110 that there is a possible problem (e.g. missing information). A red exclamation point indicates to the medical practitioner 110 that there is a "problem" that needs to be addressed.

Figure 11A:
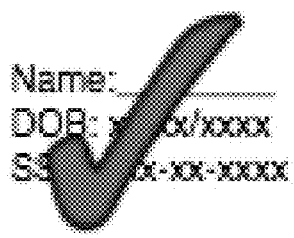
FIGS. 11A-11G show exemplary graphics that can be incorporated into a graphical user interface.
Figure 11B:
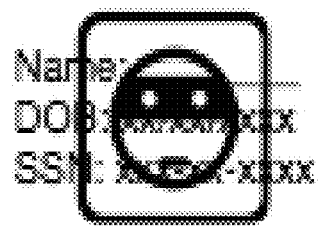
Figure 11C:
Figure 11D:
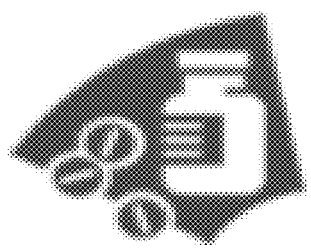
Figure 11E:
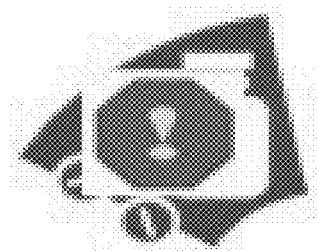
Figure 11F:
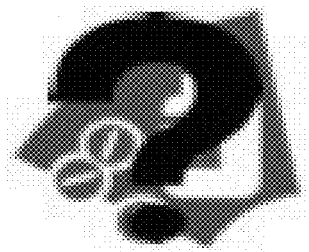
Figure 11G:
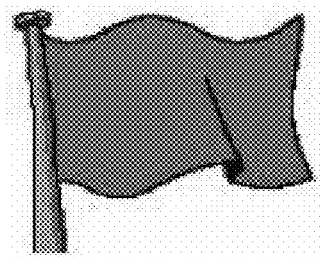

FIGS. 11A-11G show exemplary graphics that can be incorporated into the graphical user interface. FIG. 11A shows an exemplary graphic checkmark indicating that there is no problem. FIG. 11B shows an exemplary graphic "thief" emoticon indicating "stolen." FIG. 11C shows an exemplary graphic exclamation point (and a stop sign) indicating that there is a problem. FIG. 11D shows an exemplary graphic that would indicate "drugs." This might be used in combination with a checkmark (not shown) to indicate that there is no problem with drugs, an exclamation point (shown in FIG. 11E) to indicate that there was a problem with drugs, or with a question mark (shown in FIG. 11F) to indicate that more information is necessary or that there may be a problem with drugs. FIG. 11G shows a general "flag." These graphics are meant to be exemplary and are not meant to limit the scope of the invention.

A PAFP Method

Figure 12:
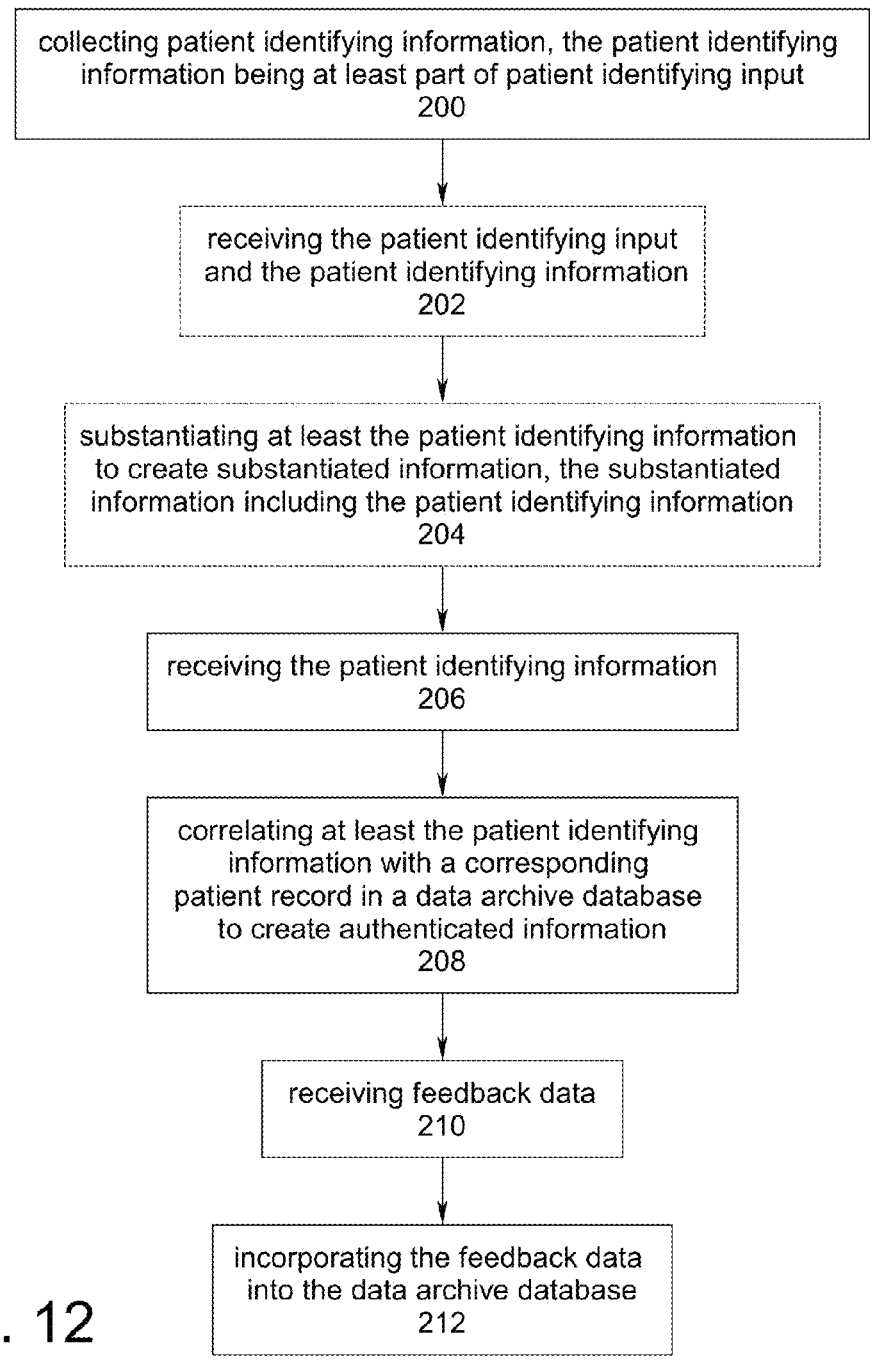
FIG. 12 is a high level flow chart of a preferred exemplary PAFP method.

FIG. 12 shows a simplified patient authentication fraud prevention method. Although shown as a linear process, it should be noted that it is can be considered circular or iterative (in that the correlation subsystem 136 searches the data archive database 150 and the feedback data 148 is used to augment and enhance the data archive database 150). Further, multiple medical practitioners 110 may use the PAFP system 100 simultaneously. Accordingly, although the terms "first," "second," and so forth are used, the process may begin at a different step and/or optional steps may be skipped.

The first step of the PAFP method is collecting patient identifying information 200, the patient identifying information being at least part of patient identifying input. This step may include collecting patient identifying information from at least one medical practitioner via a medical practitioner interaction subsystem.

The second step is receiving the patient identifying input and the patient identifying information 202. The third step is substantiating at least the patient identifying information to create substantiated information 204, the substantiated information including the patient identifying information. It should be noted that the second and third steps are optional.

The fourth step is receiving the patient identifying information 206. The patient identifying information may be part of the patient identifying input from the first step or part of the substantiated information from the third step. The fifth step is correlating at least the patient identifying information with a corresponding patient record in a data archive database to create authenticated information 208. An additional step includes providing the authenticated data to at least one medical practitioner via a medical practitioner interaction subsystem as a graphical display.

The sixth step is receiving feedback data 210. The seventh step is incorporating the feedback data into the data archive database 212. This step may include receiving feedback data from at least one medical practitioner via a medical practitioner interaction subsystem.

It should be noted that these steps may be controlled, directed, or implemented by a system processing device 130. It should be noted that these steps may be implemented using PAFP systems 100 as shown and described herein.

Comparisons to Known Systems and Methods

Many emergency department personnel rely on intuition and/or questioning techniques to uncover fraud. The problem with these techniques, however, is the inherent lack of objectivity. Some hospitals have utilized insurance verification software systems that verify a patient's identifying input (e.g. name, date of birth, social security number, address, etc.). The verified patient identifying input obtained from these insurance verification software systems, however, tends to stay with the billing and registration department. Additionally, the verified patient identifying input that is output from the insurance verification software system is sometimes not finalized for days, making no impact on the care and prescription decisions of emergency department personnel treating patients (medical decision making).

The fraud prevention and complex event processing systems discussed in the references set forth in the Background do not meet the needs of healthcare entities. This is especially true in regard to the needs of fast paced healthcare entities (such as emergency departments) where patient volume, patient anonymity, and legal constraints make for an environment with special fraud vulnerabilities.

It is to be understood that the inventions, examples, and embodiments described herein are not limited to particularly exemplified materials, methods, and/or structures. Further, all foreign and/or domestic publications, patents, and patent applications cited herein, whether supra or infra, are hereby incorporated by reference in their entirety.

The terms and expressions that have been employed in the foregoing specification are used as terms of description and not of limitation, and are not intended to exclude equivalents of the features shown and described. While the above is a complete description of selected embodiments of the present invention, it is possible to practice the invention use various alternatives, modifications, adaptations, variations, and/or combinations and their equivalents. It will be appreciated by those of ordinary skill in the art that any arrangement that is calculated to achieve the same purpose may be substituted for the specific embodiment shown. It is also to be understood that the following claims are intended to cover all of the generic and specific features of the invention herein described and all statements of the scope of the invention which, as a matter of language, might be said to fall there-between.

What is claimed is:

1. A patient authentication fraud prevention system accessible by at least one medical practitioner via a medical practitioner interaction subsystem, said system comprising:
    (a) a searchable data archive database stored in a non-transitory machine-readable storage medium, said searchable data archive having stored patient records of data pertaining to patients, said data archive database accessible by a correlation subsystem and a feedback subsystem;
    (b) said correlation subsystem for receiving patient identifying information as input from a first medical practitioner and for correlating said patient identifying information with a corresponding patient record in said data archive database to create authenticated information to be provided to a second medical practitioner who has the ability to address patient fraud based on the authenticated information; and
    (c) said feedback subsystem for receiving feedback data from a third medical practitioner, said feedback data being incorporated into said data archive database.

2. The system of claim 1 wherein said patient identifying information is at least part of substantiated information or at least part of patient identifying input.

3. The system of claim 1 further comprising a collection subsystem for collecting said patient identifying information as at least part of patient identifying input from said first medical practitioner via a medical practitioner interaction subsystem.

4. The system of claim 1 further comprising a substantiation subsystem for receiving patient identifying information as input from said first medical practitioner and for substantiating said patient identifying information to create substantiated information to be transmitted to said correlation subsystem, said substantiated information including said patient identifying information.

5. The system of claim 1 further comprising an alert subsystem for monitoring patient records in said data archive database and providing alert data to set a flag if a predetermined threshold has been met.

6. The system of claim 1 further comprising:
    (a) a collection subsystem for collecting said patient identifying information from said first medical practitioner via a medical practitioner interaction subsystem, said patient identifying information being at least part of patient identifying input to be transmitted to a substantiation subsystem; and
    (b) said substantiation subsystem for receiving patient identifying information as input from said collection subsystem, said substantiation subsystem for substantiating said patient identifying information to create substantiated information to be transmitted to said correlation subsystem, said substantiated information including said patient identifying information.

7. The system of claim 1, said authenticated data to be provided to a second medical practitioner via a medical practitioner interaction subsystem as a graphical display.

8. The system of claim 1 wherein said first medical practitioner is the same as said second medical practitioner, said second medical practitioner is the same as said third medical practitioner, said third medical practitioner is the same as said first medical practitioner, or said first medical practitioner, said second medical practitioner, and said third medical practitioner are all the same medical practitioner.

9. The system of claim 1, said authenticated information being at least two authenticated information selected from the group consisting of:
   (a) invalid, non-correlated authenticated information;
   (b) invalid, correlated authenticated information;
   (c) valid, non-correlated authenticated information;
   (d) valid, correlated authenticated information;
   (e) valid, but stolen, non-correlated authenticated information; and
   (f) valid, but stolen, correlated authenticated information.

10. The system of claim 1 wherein said patient authentication fraud prevention system is a program residing in a non-transitory machine-readable storage medium and implementable by a processor.

11. The system of claim 1 further comprising a substantiation subsystem for receiving patient identifying information as input from said first medical practitioner and for substantiating said patient identifying information to create substantiated information to be transmitted to said correlation subsystem, said substantiated information including said patient identifying information, said substantiated information indicating whether said patient identifying information is invalid, valid, or valid, but stolen, and said authenticated information providing information about patient behaviors or patient problems to said second medical practitioner.

12. A patient authentication fraud prevention system accessible by at least one medical practitioner via at least one medical practitioner interaction subsystem, said system comprising:
   (a) a searchable data archive database stored in a non-transitory machine-readable storage medium, said data archive database having stored patient records of data pertaining to patients, said data archive database accessible by a correlation subprogram and a feedback subprogram;
   (b) a collection subprogram residing in a non-transitory machine-readable storage medium and implementable by a processor, said collection subprogram for collecting said patient identifying information from a first medical practitioner via a medical practitioner interaction subsystem, said patient identifying information being at least part of patient identifying input to be transmitted to a substantiation subprogram;
   (c) said substantiation subprogram residing in a non-transitory machine-readable storage medium and implementable by a processor, said substantiation subprogram for receiving patient identifying information as input from said collection subprogram, said substantiation subsystem for substantiating said patient identifying information to create substantiated information to be transmitted to said correlation subprogram, said substantiated information including said patient identifying information;
   (d) said correlation subprogram residing in a non-transitory machine-readable storage medium and implementable by a processor, said correlation subprogram for receiving patient identifying information as input from said substantiation subprogram and for correlating said patient identifying information with a corresponding patient record in said data archive database to create authenticated information to be provided to a second medical practitioner who has the ability to address patient fraud based on the authenticated information; and
   (e) a feedback subprogram residing in a non-transitory machine-readable storage medium and implementable by a processor, said feedback subprogram for receiving feedback data from a third medical practitioner, said feedback data being incorporated into said data archive database.

13. The system of claim 12 further comprising an alert subprogram, residing in a non-transitory machine-readable storage medium and implementable by a processor, said alert subprogram for monitoring patient records in said data archive database and providing alert data to set a flag if a predetermined threshold has been met.

14. The system of claim 12, said authenticated data to be provided to a second medical practitioner via a medical practitioner interaction subsystem as a graphical display.

15. The system of claim 12 wherein said first medical practitioner is the same as said second medical practitioner, said second medical practitioner is the same as said third medical practitioner, said third medical practitioner is the same as said first medical practitioner, or said first medical practitioner, said second medical practitioner, and said third medical practitioner are all the same medical practitioner.

16. The system of claim 12, said substantiated information being at least one substantiated information selected from the group consisting of:
   (a) invalid substantiated information;
   (b) valid substantiated information; and
   (c) valid, but stolen substantiated information.

17. The system of claim 12, said authenticated information being at least one authenticated information selected from the group consisting of:
   (a) invalid, non-correlated authenticated information;
   (b) invalid, correlated authenticated information;
   (c) valid, non-correlated authenticated information;
   (d) valid, correlated authenticated information;
   (e) valid, but stolen, non-correlated authenticated information; and
   (f) valid, but stolen, correlated authenticated information.

18. The system of claim 12:
   (a) said substantiation subsystem for substantiating said patient identifying information to create substantiated information indicating whether said patient identifying information is invalid, valid, or valid, but stolen; and
   (b) said correlation subprogram creating authenticated information that provides information about patient behaviors or patient problems to said second medical practitioner.

19. A computer-implemented patient authentication fraud prevention method, said method comprising the steps of:
   (a) collecting patient identifying information using at least one computer, said patient identifying information being at least part of patient identifying input;

(b) receiving said patient identifying input and said patient identifying information, and substantiating at least said patient identifying information to create substantiated information, said substantiated information including said patient identifying information;

(c) receiving said substantiated information and said patient identifying information, and correlating at least said patient identifying information with a corresponding patient record in a data archive database to create authenticated information; and (d) receiving feedback data from a medical practitioner, and incorporating said feedback data into said data archive database.

20. The method of claim 9, said step of collecting patient identifying information further comprising collecting patient identifying information from at least one medical practitioner via a medical practitioner interaction subsystem.

21. The method of claim 19 further comprising the step of providing said authenticated data to at least one medical practitioner via a medical practitioner interaction subsystem as a graphical display, said medical practitioner having the ability to address patient fraud based on the authenticated information.

22. The method of claim 19, said step of receiving feedback data further comprising receiving feedback data from at least one medical practitioner via a medical practitioner interaction subsystem.

23. The method of claim 19 further comprising the steps of monitoring patient records in said data archive database and providing alert data to set a flag if a predetermined threshold has been met.

24. The method of claim 19 being controlled by a system processing device.

25. The method of claim 19 further comprising the steps of:

(a) substantiating at least said patient identifying information to create substantiated information indicating whether said patient identifying information is invalid, valid, or valid, but stolen; and (b) correlating at least said patient identifying information with a corresponding patient record in a data archive database to create authenticated information that provides information about patient behaviors or problems.

* * * * *